(12) United States Patent
McLuen et al.

(10) Patent No.: US 12,133,805 B2
(45) Date of Patent: Nov. 5, 2024

(54) BONE FUSION DEVICE, SYSTEM AND METHOD

(71) Applicants: Gary R. McLuen, Port Townsend, WA (US); Daniel R. Baker, Seattle, WA (US)

(72) Inventors: Gary R. McLuen, Port Townsend, WA (US); Daniel R. Baker, Seattle, WA (US)

( * ) Notice: Subject to any disclaimer, the term of this patent is extended or adjusted under 35 U.S.C. 154(b) by 0 days.

(21) Appl. No.: 17/019,017

(22) Filed: Sep. 11, 2020

(65) Prior Publication Data

US 2021/0068959 A1    Mar. 11, 2021

Related U.S. Application Data

(60) Provisional application No. 62/898,668, filed on Sep. 11, 2019.

(51) Int. Cl.
*A61F 2/44* (2006.01)
*A61F 2/30* (2006.01)
*A61F 2/46* (2006.01)

(52) U.S. Cl.
CPC ............... *A61F 2/447* (2013.01); *A61F 2/30* (2013.01); *A61F 2/4611* (2013.01); *A61F 2002/30392* (2013.01); *A61F 2002/30471* (2013.01); *A61F 2002/30507* (2013.01); *A61F 2002/3054* (2013.01); *A61F 2002/30579* (2013.01); *A61F 2002/30622* (2013.01); *A61F 2002/4627* (2013.01); *A61F 2002/4688* (2013.01)

(58) Field of Classification Search
CPC .. A61F 2002/30471; A61F 2002/30507; A61F 2002/3054; A61F 2002/30579; A61F 2002/30622; A61F 2002/4627; A61F 2/30; A61F 2/40; A61F 2/442; A61F 2/44
See application file for complete search history.

(56) References Cited

U.S. PATENT DOCUMENTS 3,176,682 A * 4/1965 Wexler ............... A61B 1/32
                                              600/219
4,484,570 A   11/1984 Sutter et al.
(Continued)

FOREIGN PATENT DOCUMENTS

FR          2717068 A1      9/1995

OTHER PUBLICATIONS

PCT Notification Concerning Transmittal of International Preliminary Report on Patentability (Chapter 1 of the Patent Cooperation Treaty), mailed Mar. 24, 2022, in International Application No. PCT/US2020/050542.

(Continued)

*Primary Examiner* — Christopher D. Prone
(74) *Attorney, Agent, or Firm* — Haverstock & Owens, A Law Corporation

(57) ABSTRACT

A bone fusion method, system and device for insertion between bones that are to be fused together in order to replace degenerated discs and/or bones, for example, the vertebrae of a spinal column. The bone fusion device includes a body and an extendable plate. The bone fusion device is able to be inserted between or replace the vertebrae by using a minimally invasive procedure wherein the dimensions and/or other characteristics of the bone fusion device are selectable based on the type of minimally invasive procedure.

13 Claims, 23 Drawing Sheets

(56) References Cited

U.S. PATENT DOCUMENTS

| | | | |
|---|---|---|---|
| 5,190,393 | A | 3/1993 | Svensson |
| 5,522,899 | A | 6/1996 | Michelson |
| 8,444,697 | B1 | 5/2013 | Butler et al. |
| 10,016,284 | B2 * | 7/2018 | Moskowitz ........ A61B 17/0642 |
| 2003/0195514 | A1 * | 10/2003 | Trieu .................... A61F 2/4611 |
| | | | 606/279 |
| 2009/0299478 | A1 | 12/2009 | Carls et al. |
| 2010/0292737 | A1 | 11/2010 | Suh |
| 2014/0277500 | A1 * | 9/2014 | Logan ..................... A61F 2/447 |
| | | | 623/17.16 |
| 2016/0038305 | A1 | 2/2016 | Weiman |
| 2016/0206440 | A1 | 7/2016 | DeRidder et al. |
| 2018/0064551 | A1 | 3/2018 | Stein et al. |
| 2019/0254838 | A1 * | 8/2019 | Miller ................... A61F 2/4455 |

OTHER PUBLICATIONS

International Search Report and Written Opinion from International Application No. PCT/US20/50542 dated Dec. 21, 2020.

\* cited by examiner

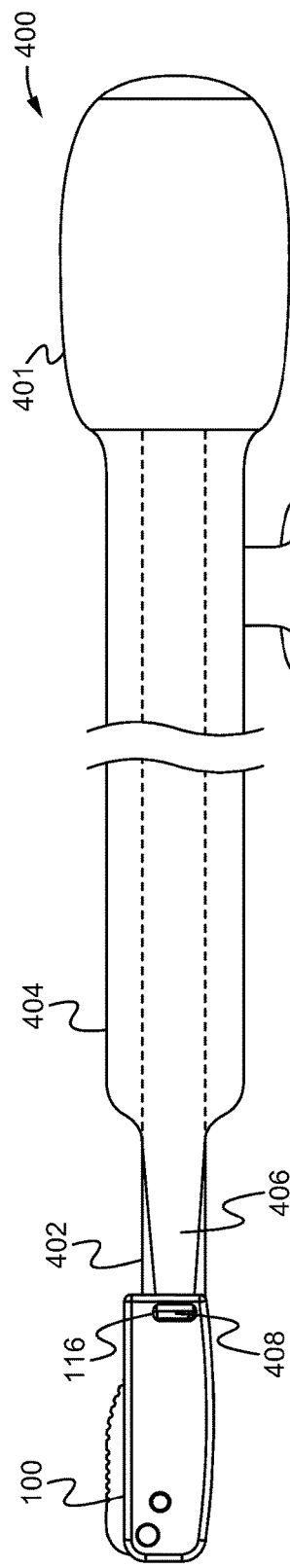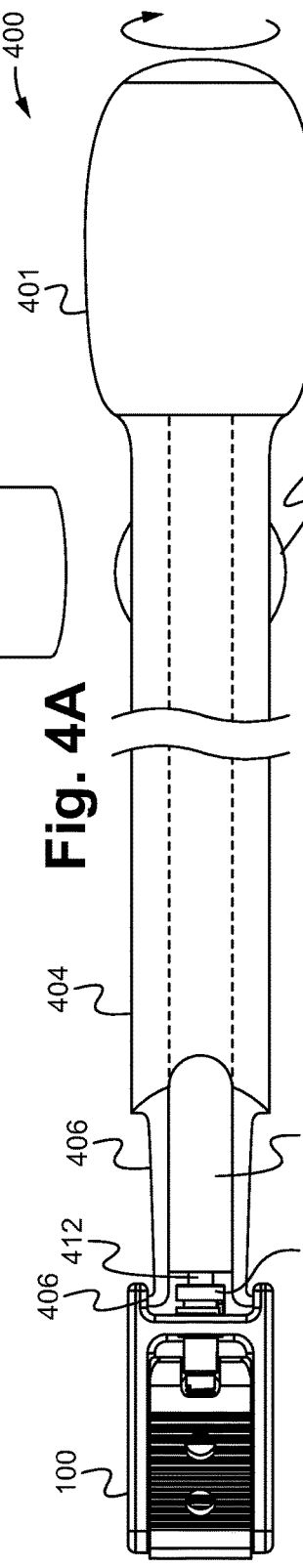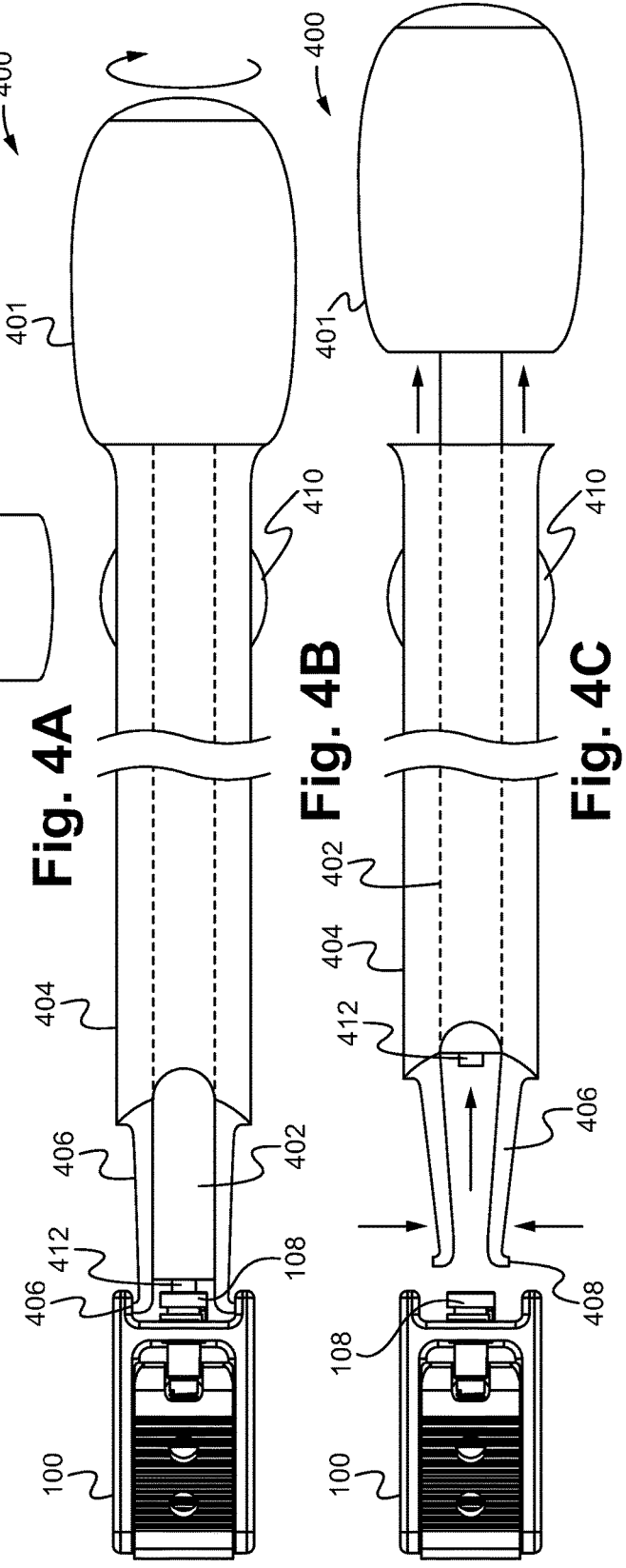

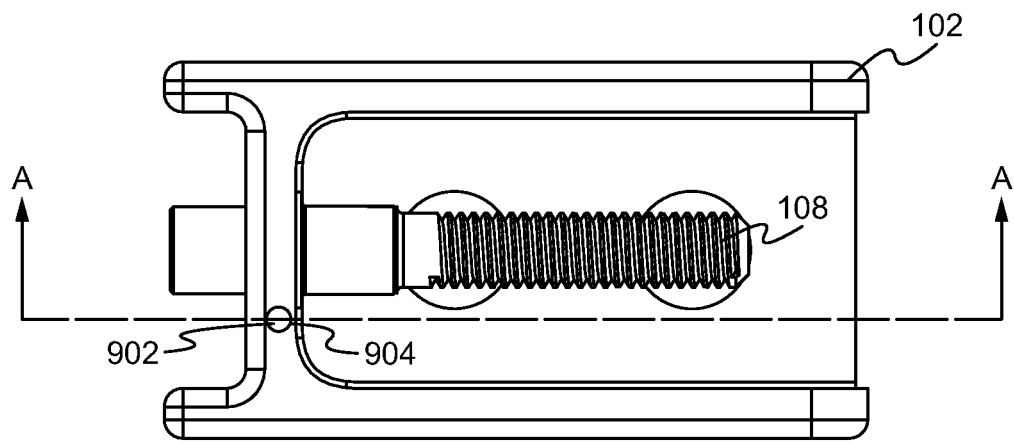
Fig. 9A
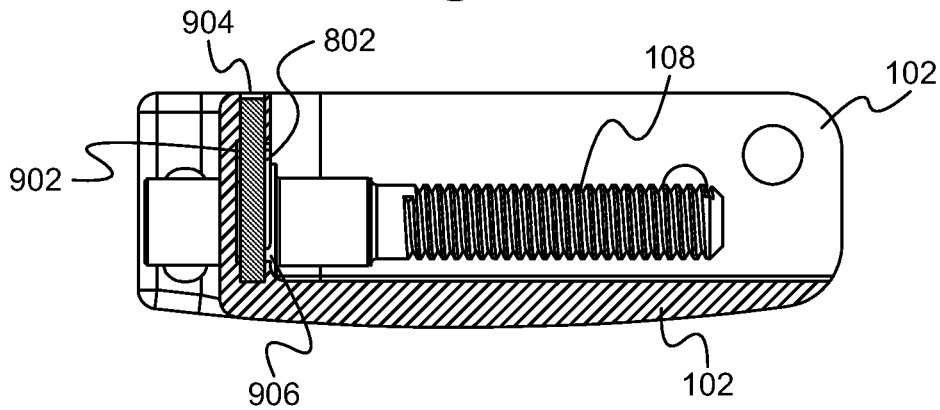
Fig. 9B
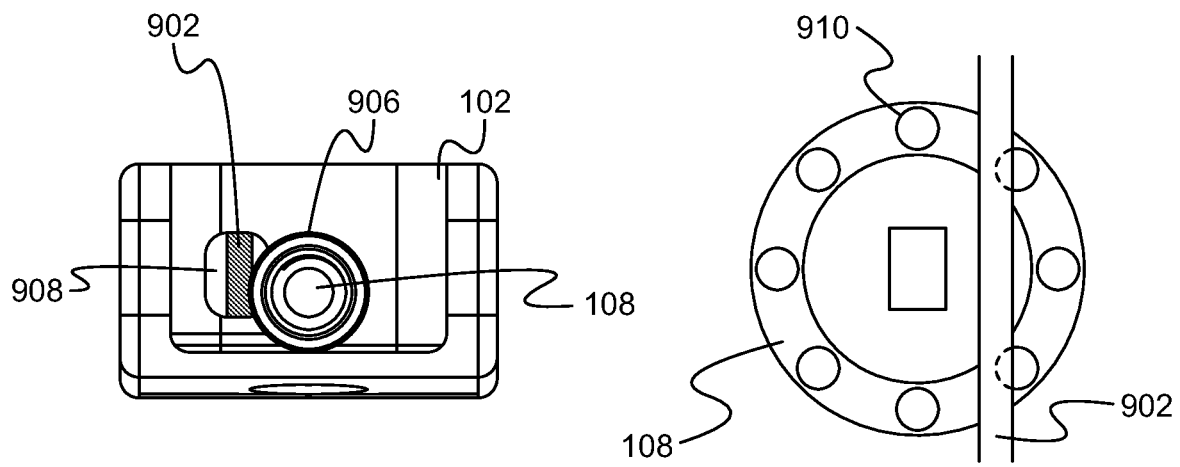
Fig. 9C
Fig. 9D

BONE FUSION DEVICE, SYSTEM AND METHOD

RELATED APPLICATIONS

This Application claims priority under 35 U.S.C. 119 (e) of the U.S. Provisional Application Ser. No. 62/898,668, filed Sep. 11, 2019, and entitled "BONE FUSION DEVICE, SYSTEM AND METHOD," which is hereby incorporated by reference.

FIELD OF THE INVENTION

This invention relates generally to bone fusion devices. More specifically, the present invention relates to devices for fusing vertebrae of the spine or other bones.

BACKGROUND OF THE INVENTION

The spinal column is made up of vertebrae stacked on top of one another. Between the vertebrae are discs which are gel-like cushions that act as shock-absorbers and keep the spine flexible. Injury, disease, or excessive pressure on the discs can cause degenerative disc disease or other disorders where the disc becomes thinner and allows the vertebrae to move closer together or become misaligned. Similarly, vertebrae are able to weaken due to impact or disease reducing their ability to properly distribute forces on the spine. As a result, nerves may become pinched, causing pain that radiates into other parts of the body, or instability of the vertebrae may ensue.

One method for correcting disc and/or vertebrae-related disorders is to insert a fusion cage as a replacement for and/or in between the vertebrae to act as a structural replacement for the deteriorated disc and/or vertebrae. The fusion cage is typically a hollow metal device usually made of titanium. Once inserted, the fusion cage maintains the proper separation between the vertebrae to prevent nerves from being pinched and provides structural stability to the spine. Also, the inside of the cage is filled with bone graft material which eventually fuses permanently with the adjacent vertebrae into a single unit. However, it is difficult to retain this bone graft material in the cage and in the proper positions to stimulate bone growth.

The use of fusion cages for fusion and stabilization of vertebrae in the spine is known in the prior art. U.S. Pat. No. 4,961,740 to Ray, et al. entitled, "V-Thread Fusion Cage and Method of Fusing a Bone Joint," discloses a fusion cage with a threaded outer surface, where the crown of the thread is sharp and cuts into the bone. Perforations are provided in valleys between adjacent turns of the thread. The cage can be screwed into a threaded bore provided in the bone structure at the surgical site and then packed with bone chips which promote fusion.

U.S. Pat. No. 5,015,247 to Michelson entitled, "Threaded Spinal Implant," discloses a fusion implant comprising a cylindrical member having a series of threads on the exterior of the cylindrical member for engaging the vertebrae to maintain the implant in place and a plurality of openings in the cylindrical surface.

U.S. Pat. No. 6,342,074 to Simpson entitled, "Anterior Lumbar Underbody Fusion Implant and Method For Fusing Adjacent Vertebrae," discloses a one-piece spinal fusion implant comprising a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopaedic screw to be retained entirely within the access passage.

U.S. Pat. No. 5,885,287 to Bagby entitled, "Self-tapping Interbody Bone Implant," discloses a bone joining implant with a rigid, implantable base body having an outer surface with at least one bone bed engaging portion configured for engaging between a pair of bone bodies to be joined, wherein at least one spline is provided by the bone bed engaging portion, the spline being constructed and arranged to extend outwardly of the body and having an undercut portion.

U.S. Pat. No. 6,582,467 to Teitelbaum et al. entitled, "Expandable Fusion Cage," discloses an expandable fusion cage where the surfaces of the cage have multiple portions cut out of the metal to form sharp barbs. As the cage is expanded, the sharp barbs protrude into the subcortical bone of the vertebrae to secure the cage in place. The cage is filled with bone or bone matrix material.

U.S. Pat. No. 5,800,550 to Sertich entitled, "Interbody Fusion Cage," discloses a prosthetic device which includes an inert generally rectangularly shaped support body adapted to be seated on hard end plates of vertebrae. The support body has top and bottom faces. A first peg is movably mounted in a first aperture located in the support body, and the first aperture terminates at one of the top and bottom faces of the support body. Further, the first peg projects away from the one of the top and bottom faces and into an adjacent vertebra to secure the support body in place relative to the vertebra.

U.S. Pat. No. 6,436,140 to Liu et al. entitled, "Expandable Interbody Fusion Cage and Method for Insertion," discloses an expandable hollow interbody fusion device, wherein the body is divided into a number of branches connected to one another at a fixed end and separated at an expandable end. The expandable cage may be inserted in its substantially cylindrical form and may be expanded by movement of an expansion member to establish lordosis of the spine. An expansion member interacts with the interior surfaces of the device to maintain the cage in the expanded condition and provide a large internal chamber for receiving bone in-growth material.

These patents all disclose fusion cage devices that can be inserted between vertebrae of the spine in an invasive surgical procedure. Such an invasive surgical procedure requires a long recovery period.

SUMMARY OF THE INVENTION

A bone fusion method, system and device for insertion between bones that are to be fused together in order to replace degenerated discs and/or bones, for example, the vertebrae of a spinal column. The bone fusion device includes a body and an extendable plate. The bone fusion device is able to be inserted between or replace the vertebrae by using a minimally invasive procedure wherein the dimensions and/or other characteristics of the bone fusion device are selectable based on the type of minimally invasive procedure. As a result, the bone fusion device, system and method is able to customized to the needs of the surgeon and patient thereby increasing the effectiveness and safety of the bone fusion procedures.

A first aspect is directed to a bone fusion device for insertion into a desired location. The bone fusion device comprises a body having an interior cavity, a plate having a first end that is pivotably coupled to a back end of the body at a pivot point and a second end that is opposite the first end, wherein the plate is configured to selectively move from a retracted position having the second end within the interior cavity to an extended position having the second end outside of the interior cavity by pivoting about the pivot point, a positioning component located partially within the interior cavity and an extending block coupled with the positioning component and configured to slide within the interior cavity of the body based on rotation of the positioning component thereby causing the plate to pivot between the retracted position and the extended position.

A second aspect is directed to a bone fusion device for insertion into a desired location. The bone fusion device comprises a body having a front wall and an interior cavity, wherein the front wall includes a positioning aperture surrounded by one or more lock indentations, a plate configured to selectively move from a retracted position within the interior cavity to an extended position at least partially outside of the interior cavity, a positioning component extending through the positioning aperture partially within the interior cavity, an extending block coupled with the positioning component and configured to slide within the interior cavity of the body based on rotation of the positioning component thereby causing the plate to move between the retracted position and the extended position and a locking mechanism coupled to the positioning component adjacent to the front wall and having a locking arm with a protruding locking tip, wherein the locking arm biases the locking tip such that when aligned with one of the lock indentations the locking tip slides into the one of the lock indentations and thereby resists rotation of the positioning component.

A third aspect is directed to a bone fusion system for insertion of a bone fusion device into a desired location. The system comprises a bone fusion device including a body having an interior cavity, a plate having a first end that is pivotably coupled to a back end of the body at a pivot point and a second end that is opposite the first end, wherein the plate is configured to selectively move from a retracted position having the second end within the interior cavity to an extended position having the second end outside of the interior cavity by pivoting about the pivot point, a positioning component located partially within the interior cavity, and an extending block coupled with the positioning component and configured to slide within the interior cavity of the body based on rotation of the positioning component thereby causing the plate to pivot between the retracted position and the extended position and an inserter instrument coupled to the bone fusion device, wherein the inserter instrument has a plurality of gripping arms and a sliding tube, and further wherein the gripping arms have protruding fingers that are configured to slide into gripping apertures of the body of the bone fusion device when the sliding tube slides between the gripping arms thereby pushing the protruding fingers away from each other and into the gripping apertures, and further wherein the gripping arms are biased to spring toward each other and out of the gripping apertures when the sliding tube slides out from in between the gripping arms.

BRIEF DESCRIPTION OF THE DRAWINGS

FIG. 4A illustrates a side view of a bone fusion system having an insertion tool coupled with the bone fusion device according to some embodiments.

FIG. 4B illustrates a top attached view of a bone fusion system having an insertion tool coupled with the bone fusion device according to some embodiments.

FIG. 4C illustrates a top unattached view of a bone fusion system having an insertion tool coupled with the bone fusion device according to some embodiments.

FIG. 9A illustrates a top view of an alternative embodiment of the locking mechanism according to some embodiments.

FIG. 9B illustrates a side wireframe view cross-sectional at the section A-A of an alternative embodiment of the locking mechanism according to some embodiments.

FIG. 9C illustrates a back view of an alternative embodiment of the locking mechanism according to some embodiments.

FIG. 9D illustrates a front perspective view of an alternative embodiment of the locking mechanism of FIGS. 9A-C according to some embodiments.

DETAILED DESCRIPTION

In the following description, numerous details and alternatives are set forth for purpose of explanation. However, one of ordinary skill in the art will realize that the invention can be practiced without the use of these specific details. For instance, the figures and description below often refer to the vertebral bones of a spinal column. However, one of ordinary skill in the art will recognize that some embodiments of the invention are practiced for the fusion of other bones, including broken bones and/or joints. In other instances, well-known structures and devices are shown in block diagram form in order not to obscure the description of the invention with unnecessary detail.

Figure 1A:
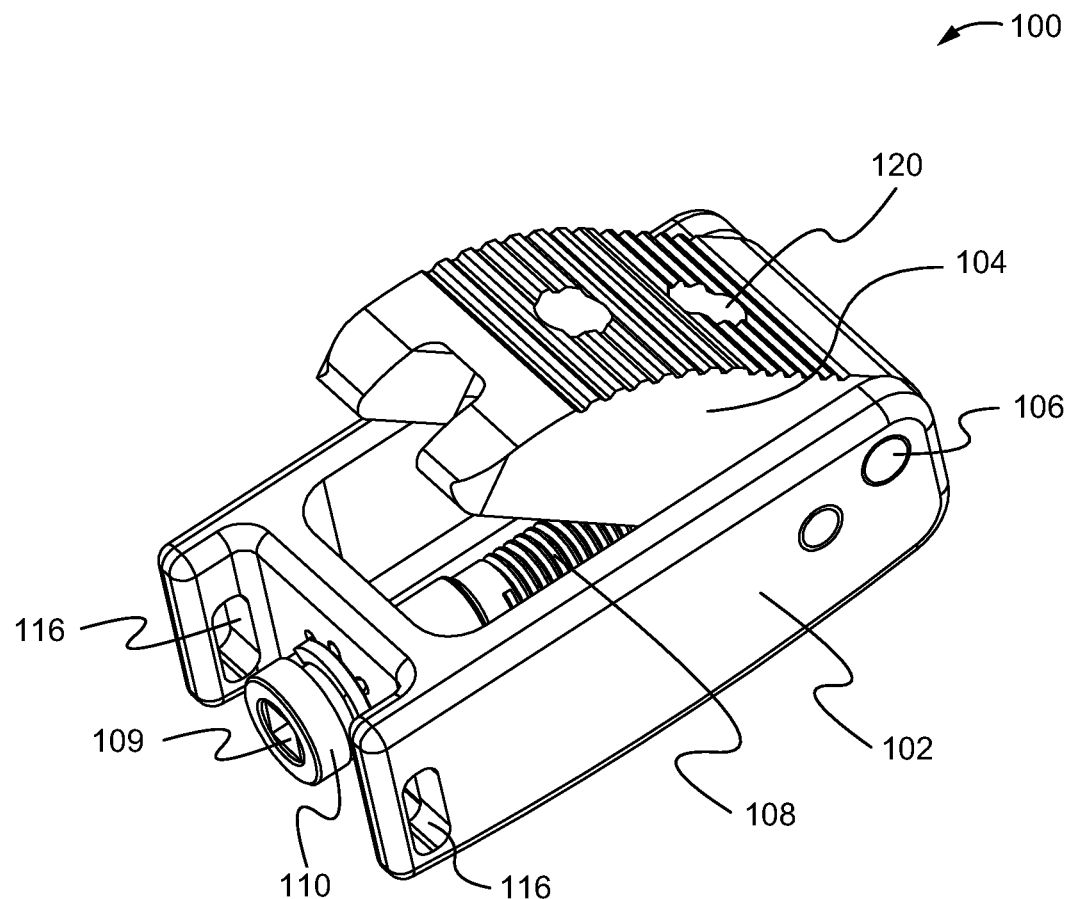
FIG. 1A illustrates a perspective view of a bone fusion device according to some embodiments.
Figure 1B:
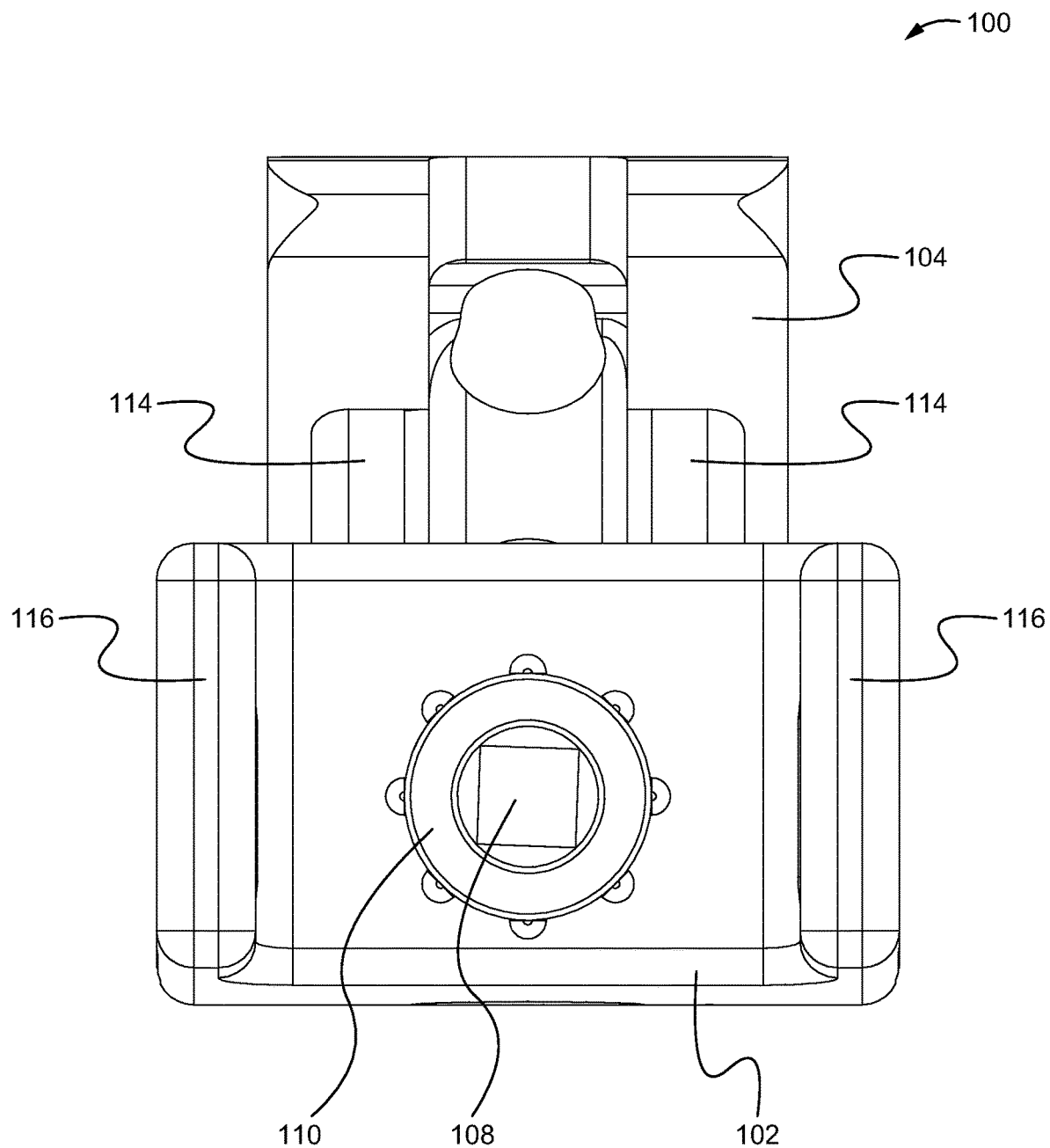
FIG. 1B illustrates a front view of a bone fusion device according to some embodiments.
Figure 1C:
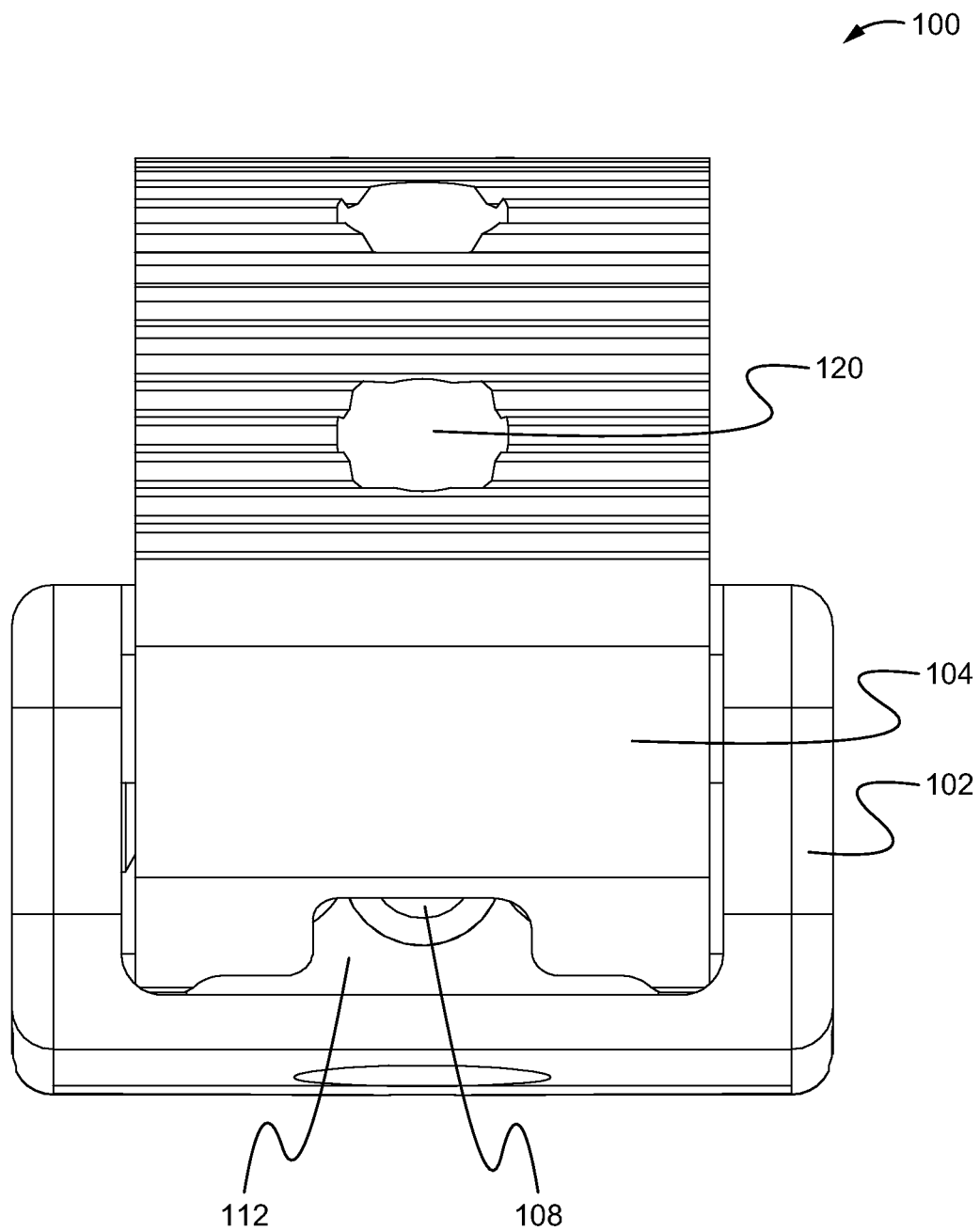
FIG. 1C illustrates a back view of a bone fusion device according to some embodiments.
Figure 1D:
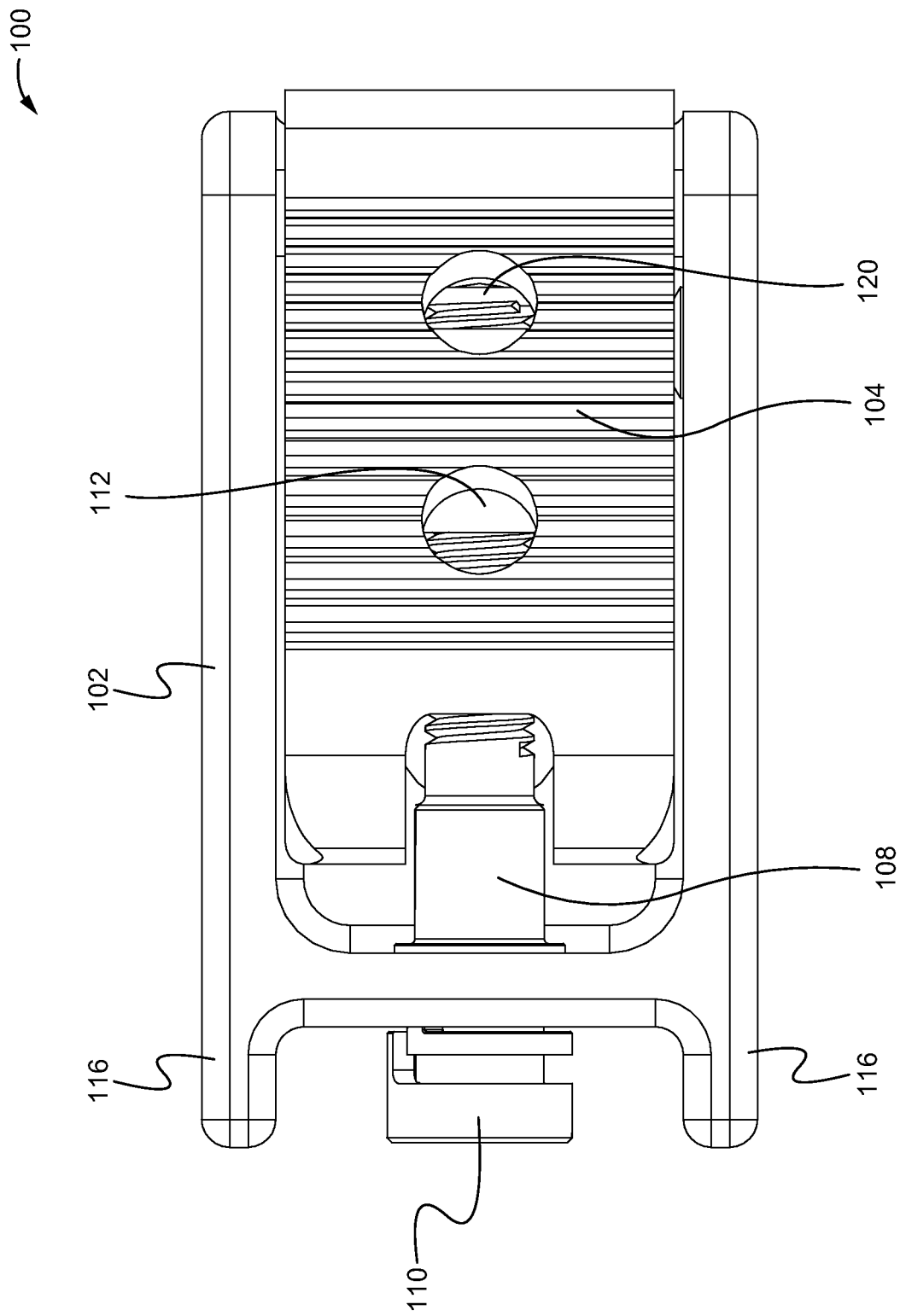
FIG. 1D illustrates a top view of a bone fusion device according to some embodiments.
Figure 1E:
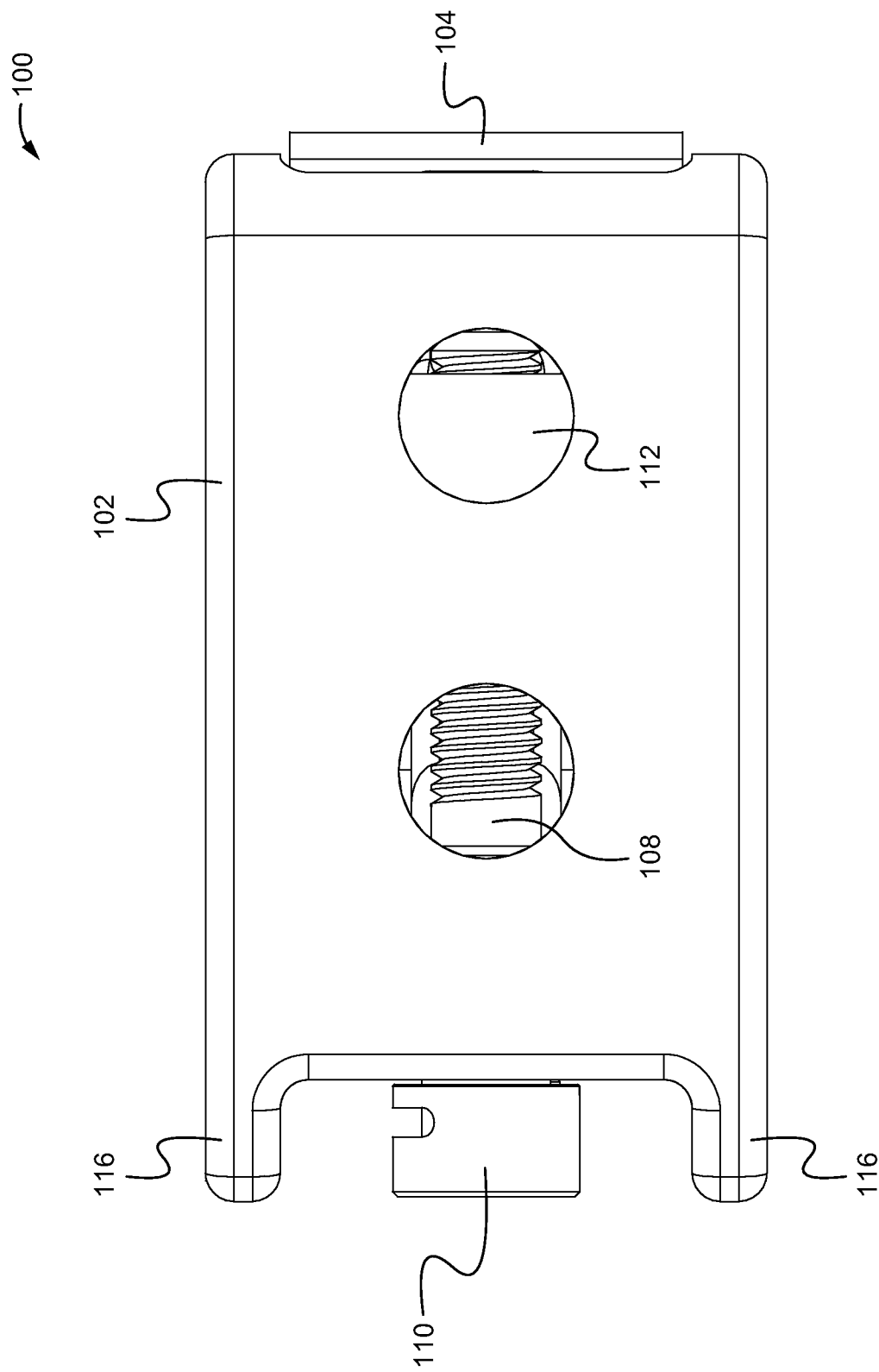
FIG. 1E illustrates a bottom view of a bone fusion device according to some embodiments.
Figure 1F:
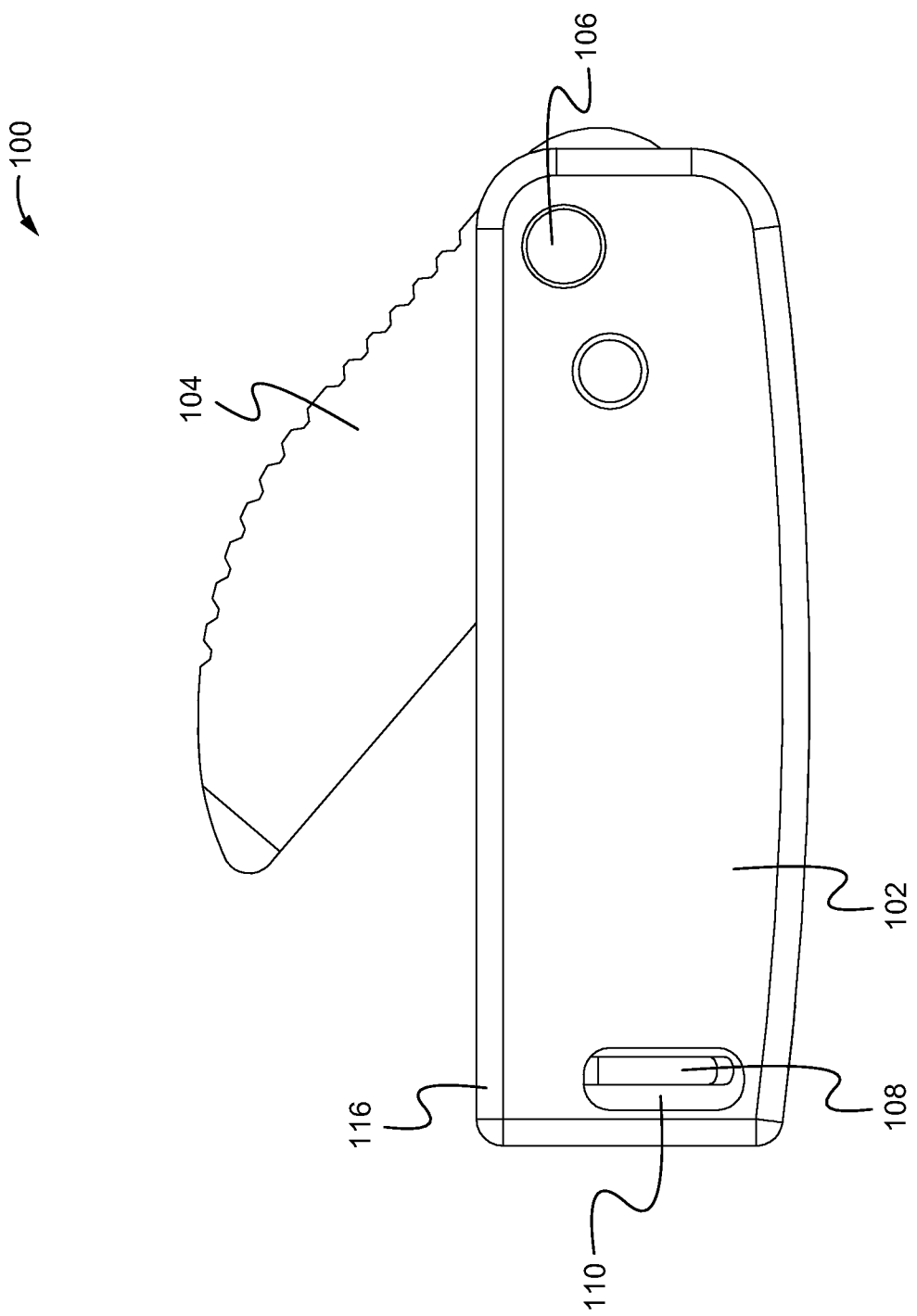
FIG. 1F illustrates a side view of a bone fusion device according to some embodiments.
Figure 2A:
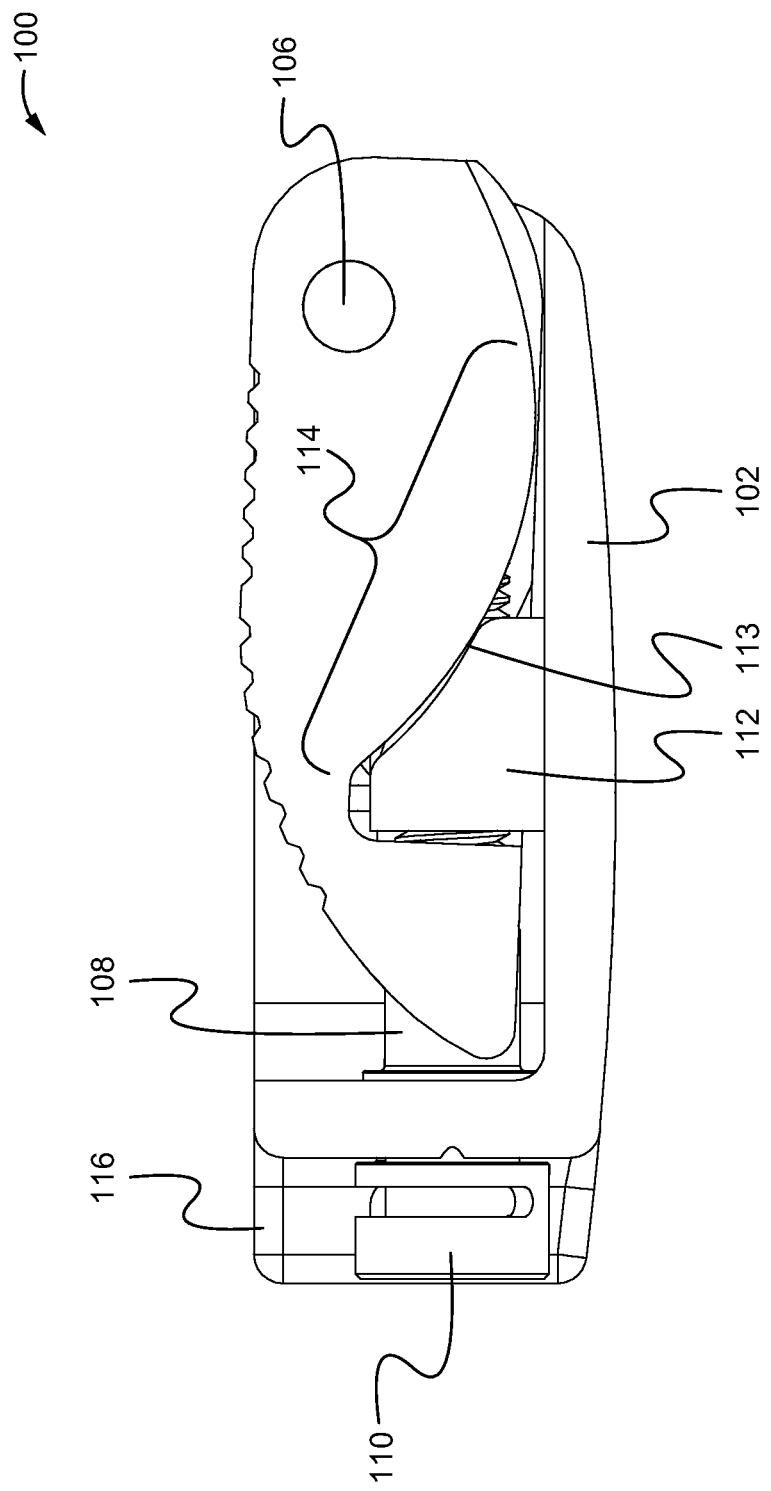
FIG. 2A illustrates a side cross sectional view of a bone fusion device in a retracted position according to some embodiments.
Figure 2B:
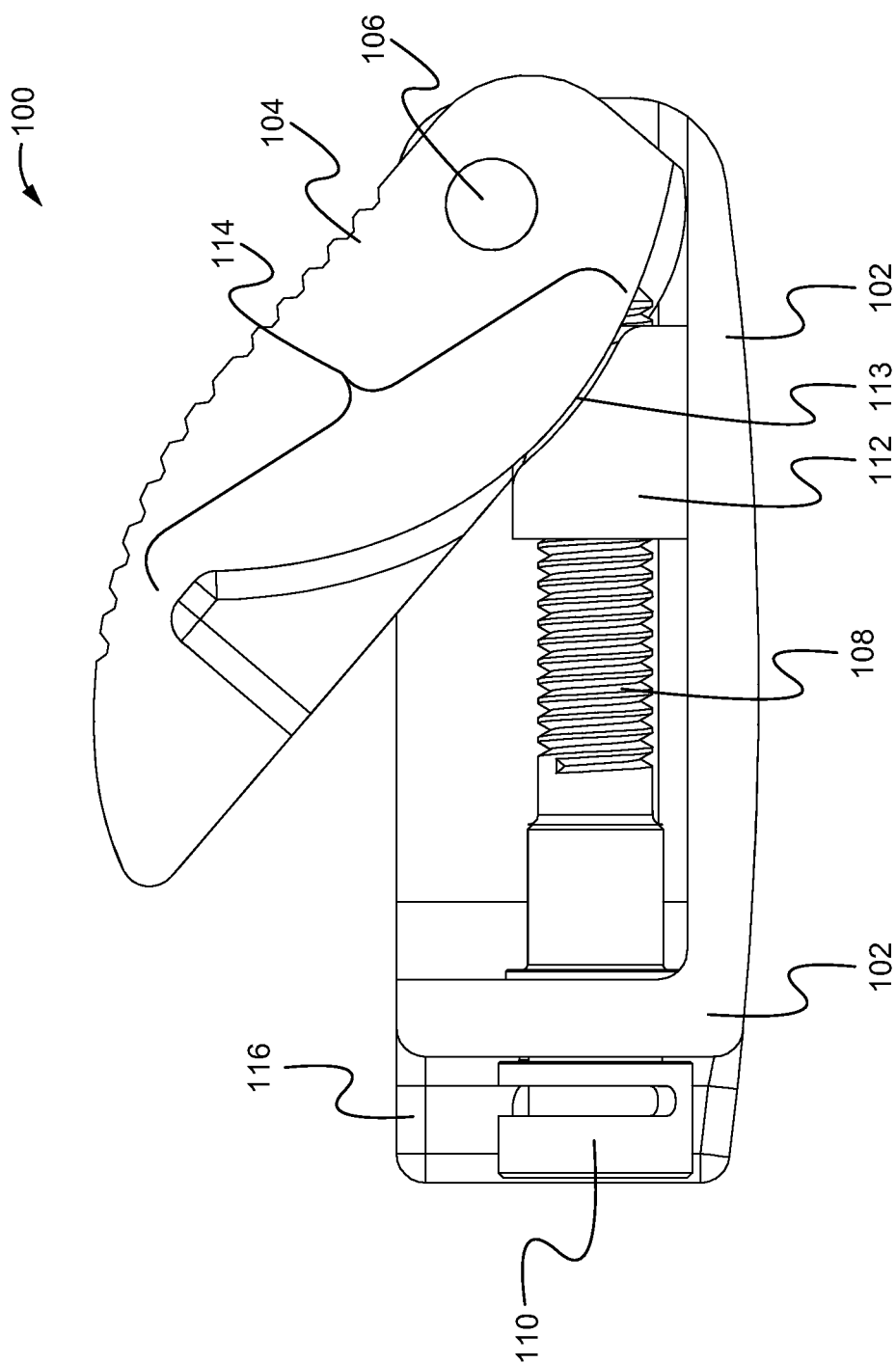
FIG. 2B illustrates a side cross sectional view of a bone fusion device in an extended position according to some embodiments.

FIGS. 1A-1F illustrate perspective, front, back, top, bottom and side views of a bone fusion device 100, respectively, according to some embodiments. FIGS. 2A and 2B illustrate side cross sectional views of the bone fusion device 100 in an extended position and a retracted position according to some embodiments. The bone fusion device 100 is able to be constructed from a high strength biocompatible material, such as titanium, which has the strength to withstand forces in the spine that are generated by a patient's body weight and daily movements. Alternatively, part of all of the bone fusion device 100 is able to be constructed from one or more of the group consisting of high strength biocompatible material or a polymer such as PEEK, PEKK, and other polymeric materials know to be biocompatible and having sufficient strength. In some embodiments, the materials used to construct the bone fusion device include using additives, such as carbon fibers for better performance of the materials under various circumstances. The base biocompatible material is often textured or coated with a porous material conducive to the growth of new bone cells on the bone fusion device 100. In some embodiments, the materials used to construct the bone fusion device include using additives, such as carbon fibers for better performance of the materials under various circumstances.

In some embodiments, the porous material or coating is able to be a three-dimensional open-celled titanium scaffold for bone and tissue growth (e.g. an OsteoSync structure). For example, the coating is able to be a osteosync structure having a mean porosity of 50-70%, pore sizes ranging from 400-700 μm, and/or a mean pore interconnectivity of 200-300 μm. Alternatively or in addition, the coating is able to be hydroxapatite, coatings with reenterent porosity for bone ingrowth and/or other coatings for both ingrowth and ongrowth of bone. Alternatively, instead of or in addition to a coating on the bone fusion device 100, the porous material is able to be integrated into the frame and component of the bone fusion device 100. The bone fusion device 100 is able to have several conduits or holes 120 which permit the bone graft material to be inserted into the device 100 and to contact the vertebral bone before or after the device 100 has been inserted between the vertebrae of the patient. The bone graft material and the surface texturing of the device 100 encourage the growth and fusion of bone from the neighboring vertebrae. The fusion and healing process will result in the bone fusion device 100 aiding in the bridging of the bone between the two adjacent vertebral bodies of the spine which eventually fuse together during the healing period.

As shown in FIGS. 1A-1E, 2A and 2B, the bone fusion device 100 comprises a body 102, a plate 104, a pin 106, a positioning component 108, a locking mechanism 110 and a sliding block 112. Alternatively, in some embodiments the locking mechanism 110 is able to be omitted (see FIG. 2C). The body 102 is able to comprise an internal cavity, a far end with apertures for receiving the pin 106 and a near end with a hole (for receiving the positioning component 108) and one or more protruding coupling rings or hoops 116 (for coupling with an insertion tool 400). At the far end of the body 102, the plate 104 is pivotably or rotatably coupled with the body 102 via the pin 106. Specifically, the pin 106 extends through both the body 102 and the plate 104 such that the plate 104 is able to pivot about the axis of the pin 106. Indeed, unlike other bond fusion devices, by enabling the rotation of the plate 104 about the pin 106 at one end of the plate 104, the device 100 is able to provide the benefit of maximizing the height to which the plate 104 is able to extend out of the body 102 while maintaining a small form factor. At the same time, the device 100 provides the advantage of enabling large amounts of bone graft or other material to be inserted into the cavity of the body 102 (e.g. before insertion, via the insertion tool; and/or via other tools) due to the large opening created by the rotation/extension of the plate 104 out of the body 102 about the pin 106.

At the near end of the body 102, the positioning component 108 is positioned through the hole in the body 102 such that the component 108 is partially inside and partially outside the body 102 and able to rotate in place within the hole. Outside the body 102, the positioning component 108 is coupled with the locking mechanism 110, which helps prevent unwanted rotating of the component 108 within the hole as described in detail below (see FIGS. 3A and 3B). Inside the body 102, the component 108 has a threaded portion that is coupled with the sliding block 112. In particular, the block 112 is able to have an internally threaded channel that is able to be threaded or screwed onto the threaded portion of the positioning component 108. Further, the positioning component 108 is able to comprise a positioning aperture 109 located on the end of the component 108 that protrudes out of the body 102. The positioning aperture 109 is configured to receive a drive/engaging mechanism an insertion tool 300 (see FIG. 4) such that the tool 300 is able to rotate or otherwise manipulate the positioning component 108. The positioning aperture 109 is able to comprise a square or numerous other shapes and sizes well known in the art. Additionally, it is contemplated that the positioning component 108 is able to be a non-rotational or other type of force generating mechanism that is able to move the extending block 112. For example, the positioning component 108 is able to be a mechanism were a non-rotational movement (e.g. in/out of the device 100) causes the movement of the extending block 112.

The plate 104 is able to be sized such that, in the retracted position (as shown in FIG. 2A), a top/outer surface of the plate 104 (e.g. partially serrated surface) is flush with or within an outer plane of the cavity of the body 102. As a result, the plate 104 does not increase the size of the device 100 by protruding out of the body 102 in the retracted position. In cross-section, as shown in FIGS. 2A and 2B, the plate 104 is able to have a substantially flat bottom plane (e.g. for sitting on the floor of the body 102) and a curving top plane (e.g. for providing a substantially parallel top extending surface even as the plate 104 rotates). Specifically, the plate 104 is able to have a thick end (with a channel for receiving the pin 106) which starts at a substantially flat angle and then gradually increases in slope downward toward the opposite end (e.g. the thinner end) ultimately coming to a rounded point at the opposite end. As a result, the cross-section profile of the plate 104 starts at a thickness at the thicker end and gets gradually thinner (e.g. at least partially at a non-linear or curved rate) toward the opposite end. Thus, the plate 104 provides the advantage of maintaining a substantially parallel topmost surface even as it rotates about the pin 106 due to its curved top surface.

Internally, the plate 102 has in inner surface with one or more angled ramps 114 for contacting the sliding block 112 as it slides along the positioning component 108. The ramps 114 are able to get gradually thicker from the start of the ramps 114 (e.g. closest to the thinner end of the plate 104) to the end of the ramps 114 (e.g. closest to the thicker end of the plate 104 that is coupled to the pin 106). As a result, when the block 112 moves down the positioning component 108 from the start of the ramps 114 to the end of the ramps 114, the block 112 contacts the increasingly thicker ramps 114 thereby causing the plate 104 to rotate about the pin 106 out of the body 102 to the extended position. In some embodiments, the ramps 114 are able to be curved (e.g. an involute curve) in order to maximize contact between the block 112 and the ramps 114. In some embodiments, the curvature of the block 112 and of the ramps 114 is able to match or be congruent for one or more portions as the block 112 moves along the positioning component 108 and presses against the ramps 114. Alternatively, one or more of the ramps 114 are able to be partially or fully linear.

Further, the plate 104 is able to have serrated edges or teeth to further increase the bone fusion device's gripping ability and therefore ability to be secured in place between the bones for both a long-term purchase and a short-term purchase. In some embodiments, the serrated edges or teeth are able to be in a triangular or form a triangular wave formation. Alternatively, the serrated edges or teeth are able to be filleted, chamfered, or comprise other teeth shapes or edge waves as are well known in the art.

The block 112 comprises an internally threaded channel (as described above) for receiving the threaded portion of the positioning component 108 and one or more angled and/or curved surfaces 113 for contacting and/or pushing against the ramps 114 of the plate 104. In particular, the angled/curved surfaces 113 are able to be concave curves that are able to substantially mate with the convex curves of the ramps 114 thereby maximizing contact area as the block 112 pushes against the ramps 114 with the angled/curved surfaces 113. Alternatively, all or portion of the angled/curved surfaces 113 are able to be linear. In some embodiments, the block 112 further comprises a hinge pin (not shown) that is substantially perpendicular to the positioning component 108 and enables the block 112 and/or its angled/curved surfaces 113 to flex or rotate up or down about the hinge pin in order to maintain greater contact with the ramps 114. Alternatively, the hinge pin is able to be omitted.

In any case, the block 112 is positioned away from the pin 106 when the plate 104 is in the retracted position. When the positioning component 108 is turned appropriately within the body 102 (e.g. via the tool 300), the threading on the extending block 112 and the positioning component 108 causes the block 112 to move down the component 108 toward the pin 106. As the block 112 moves toward the pin 106, the angled/curved surfaces 113 push against the ramps 114 of the plate 104 causing the plate 104 to rotate about the pin 106 from the retracted position to the extended position. In some embodiments, when in the fully extended position, the plate 104 extends above the body 102 at least two times the height of the body 102. To retract the plate 104, the positioning device 108 is turned in the opposite direction and the extending block 112 will travel away from the pin 106 enabling the plate 104 to move into the retracted position due to gravity or another downward force. As a result, the bone fusion device 100 provides the advantages of a compact assembly that is suitable for insertion into the patient's body through a open, or minimally invasive surgical procedure. Indeed, minimally invasive procedures minimize or eliminate the need for excessive retraction of a patient's tissues such as muscles and nerves, thereby minimizing trauma and injury to the muscles and nerves and further reducing the patient's recovery time.

Figure 2C:
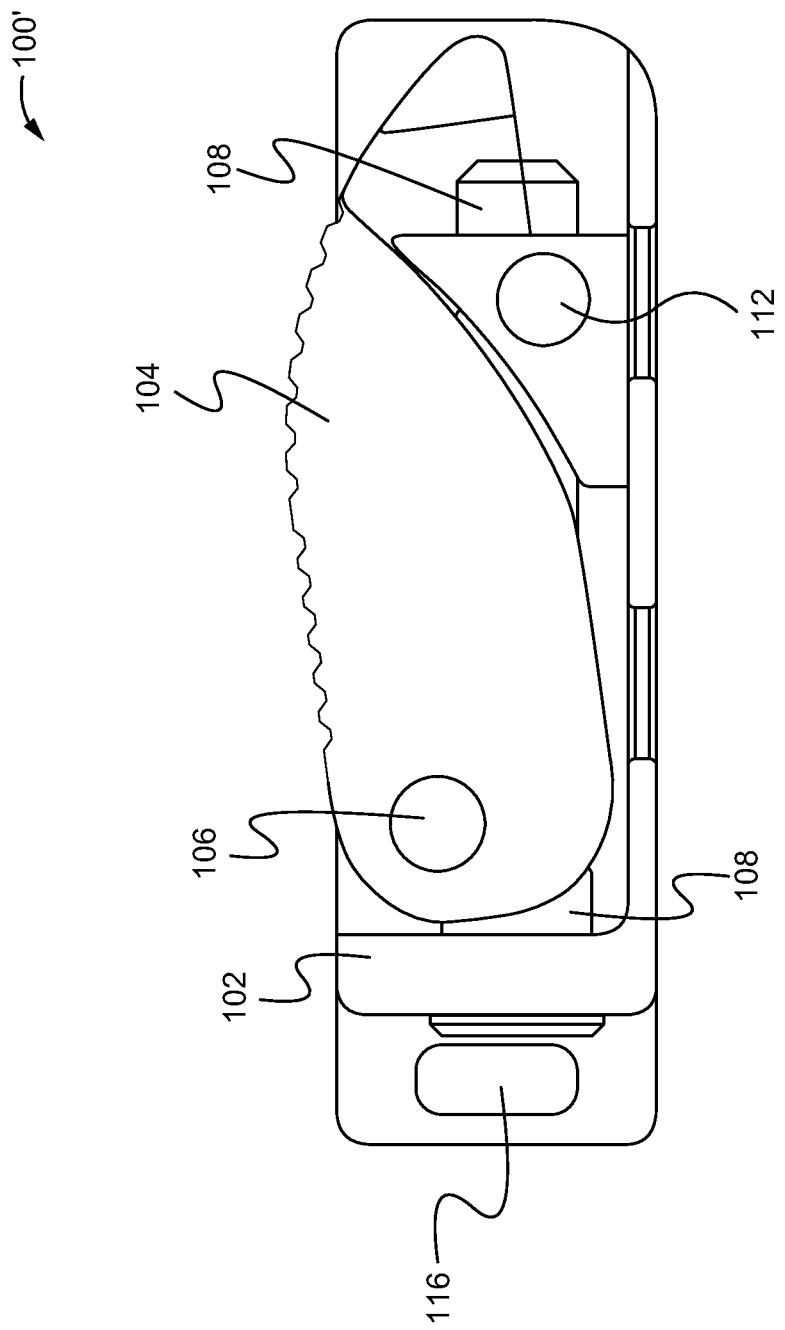
FIG. 2C illustrates a side cross sectional view of a bone fusion device according to some embodiments.

In some embodiments, the plate 104 is able to be biased with a biasing mechanism that applies the downward force needed to cause the plate 104 to retract when enabled by the position of the extending block 112. For example, one or more springs are able to be coupled to the plate 112, wherein the springs apply a retraction biasing force to the plate 104 that causes the plate to retract when enabled by the extending block 112. In some embodiments, the pin 106 is able to be positioned on the near end of the body 102 instead of the far end. In particular, FIG. 2C illustrates a cross-sectional side view of an alternate embodiment of the bone fusion device 100' having the pin 106 at the near end of the body 102 according to some embodiments. As shown in FIG. 2C, the device 100' is substantially similar in operation and structure as the device 100 except for the differences described herein. In particular, the position of the threaded portion of the component 108 and the orientation/position of the block 112 is reversed compared to the device 100. Further, the positioning component 108 is able to have a cutout or groove for receiving the pin 106 and thereby enabling the pin 106 to be positioned lower within the body 102 without the pin 106 interfering with the rotation of the component 108. Additionally, as shown in FIG. 2C the device 100' does not have a locking mechanism such that the positioning component 108 does not need to protrude as far out of the body 102 as in the device 100. Alternatively, a locking mechanism is able to be added in the same manner as in the device 100. Finally, unlike the device 100, the body 102 of the device 100' is able to have an end wall at the far end instead of the opening for the thicker end of the plate 104 in the device 100'. It is noted that one or more of the elements of the devices 100 and 100' that are shown and described separately herein are able to be incorporated into one or the other's structure.

Figure 3A:
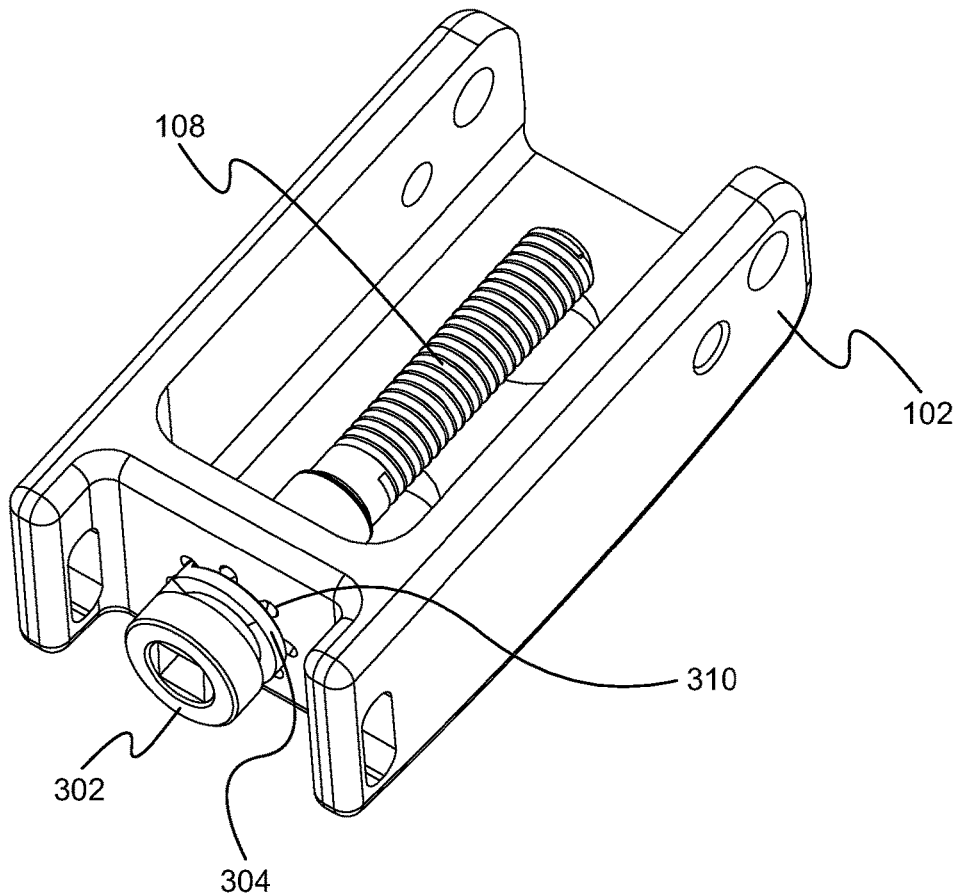
FIGS. 3A and 3B illustrate perspective and exploded perspective views of the locking mechanism according to some embodiments.
Figure 3B:
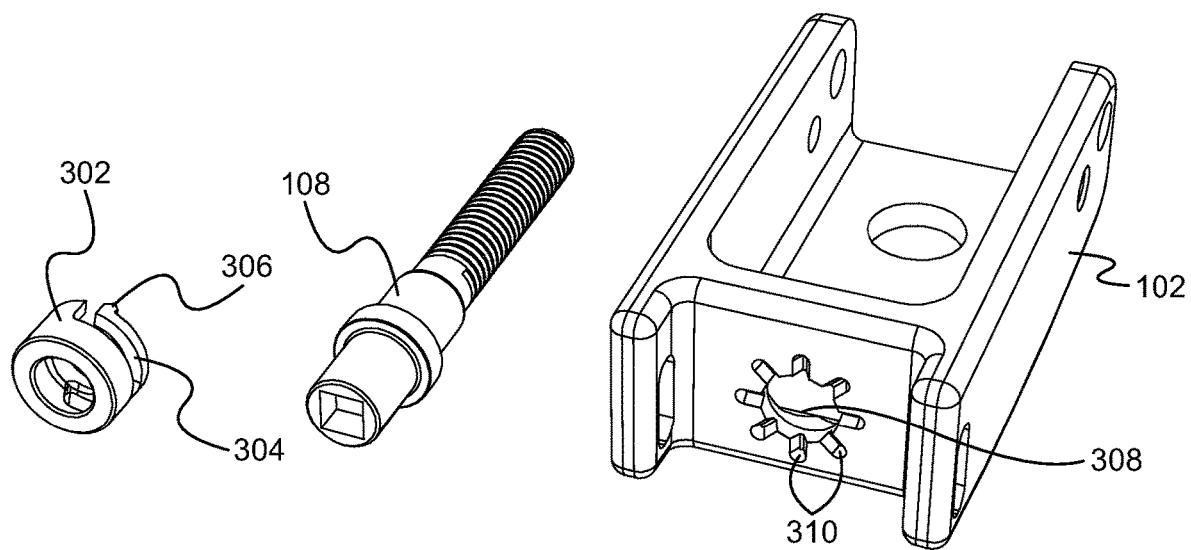

FIGS. 3A and 3B illustrate perspective and exploded perspective views of the locking mechanism 110 according to some embodiments. As shown in FIGS. 3A and 3B, the locking mechanism 110 comprises a hollow head 302 that couples around the end of the positioning component 108 and a spring arm 304 having a retention tip 306 that extends from the bottom of the hollow head 302. As a result, when the positioning component 108 is rotated within the hole 308 of the body 102 in a direction to extend the plate 104, the locking mechanism 110 is also rotated and the retention tip 306 springs into and out of a plurality of body dimples or apertures 310 in the body 102 (with the spring arm 304 providing a biasing force pushing the tip 306 into the dimples 310 when the tip 306 and one of the dimples 310 align. In particular, the tip 306 has an angled leading edge and a substantially flat trailing edge such that rotation to extend the plate 104 is more easily permitted because the angled leading edge facilitates the popping out of the tip 306 from one dimple 310 to the next dimple 310. In contrast, the flat trailing edge resists rotation to contract the plate 104 because it does not facilitate the popping out in the opposite direction of rotation. Accordingly, the locking mechanism 110 is able to provide an anti-slipping or position locking function by helping to prevent the plate 104 from undesiredly retracting once at the desired extension position. Further, the mechanism 110 provides the benefit of incremental rotation points such that an amount of rotation/extension of the plate 104 is more precisely enabled. Although in FIG. 3B eight dimples 310 are shown more or less dimples 310 are contemplated.

Figure 8A:
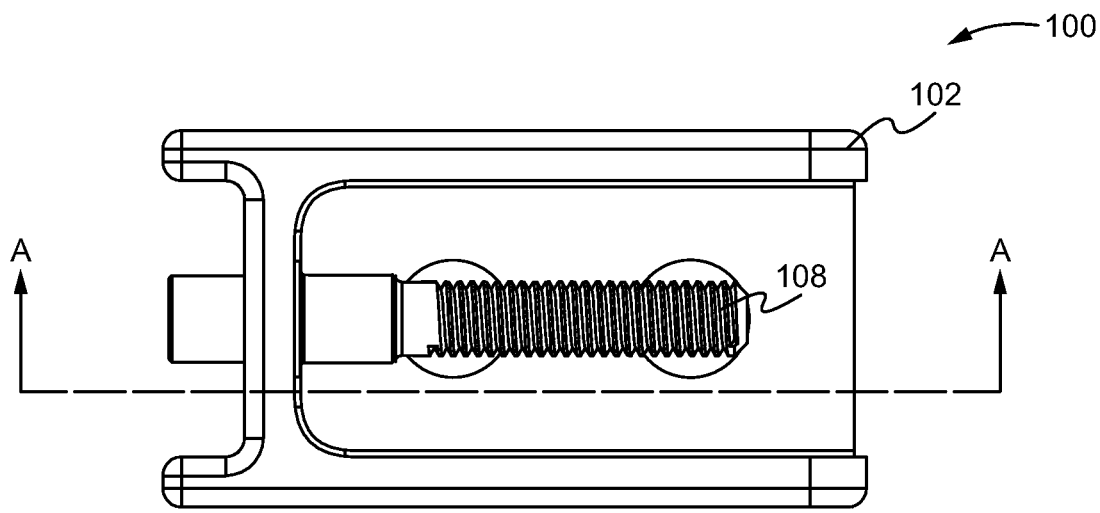
FIG. 8A illustrates a top view of an alternative embodiment of the locking mechanism according to some embodiments.
Figure 8B:
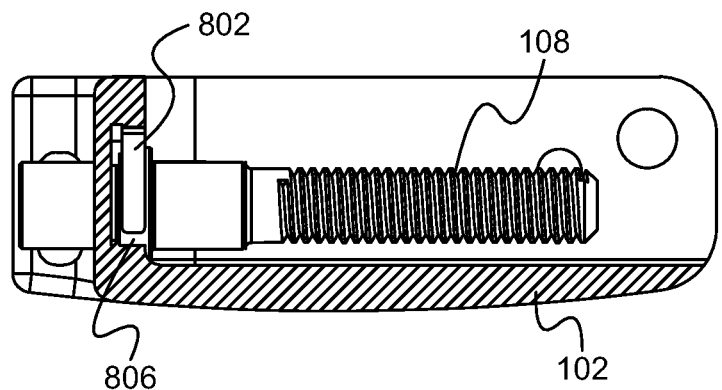
FIG. 8B illustrates a side cross-sectional at the section A-A of an alternative embodiment of the locking mechanism according to some embodiments.
Figure 8C:
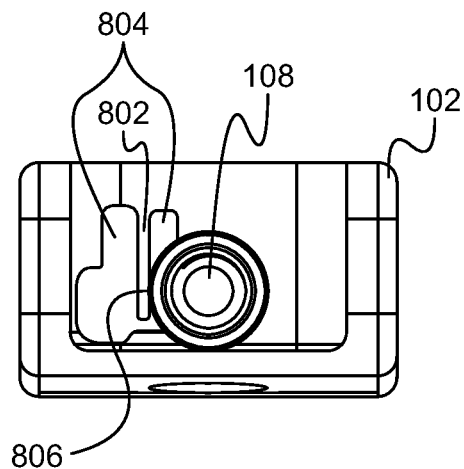
FIG. 8C illustrates a back view of an alternative embodiment of the locking mechanism according to some embodiments.

FIGS. 8A, 8B and 8C illustrate top, side cross-sectional at the section A-A and back views of an alternative embodiment of the locking mechanism 110 according to some embodiments. The device 100 of FIGS. 8A-C is able to be substantially the same as the device in FIG. 1 except for the differences described herein. As shown in FIGS. 8A, 8B and 8C, the locking mechanism 110 comprises a leaf spring 802 built into the body 102 of the device 100. In particular, a front end of the body 102 has a cavity 804 adjacent to the positioning component 108 with a leaf spring 802 protruding into the cavity 804 in contact with the side of the positioning component 108. At the same time, instead of being circular and/or smooth, the outer perimeter surface 806 of the positioning component 108 (adjacent to the spring 802) is able to comprise a plurality of flat faces such that the perimeter 806 is hexagonal, octagonal, or any number of flat faces. Further, each of the flat faces are able to be parallel and/or in contact with the spring 802 when the positioning component 108 is rotated such that the face is the closest to the spring 802.

As a result, the spring 802 is able to bias the positioning component 108 into positions where one of the faces is parallel to the spring 802 by pushing against the corners of the perimeter 806 when one of the faces is non-parallel to the spring 802. In particular, as the positioning component 108 rotates and one of the faces begins to move from parallel to the spring 802 to increasingly non-parallel to the spring 802, the corner formed by two of the faces pushes the spring 802 away from the positioning component 108 and the spring 802 resists this movement thereby resisting the rotation of the positioning component 108. In some embodiments, like in FIG. 3, the leaf spring 802 is able to have a bump and the faces of the perimeter 806 are able to have matching dimples or the leaf spring 802 is able to have a dimple and the faces of the perimeter 806 are able to have matching bumps. This further increases the biasing effect of the leaf spring 802 into the parallel positions where the bump and dimples are aligned. Alternatively, in such embodiments, the perimeter 806 is able to instead be circular or smooth because the dimples/bumps are able to replace the flat faces. In any case, like in FIG. 3, the locking mechanism 110 provides the benefit of incremental rotation points such that an amount of rotation/extension of the plate 104 is more precisely enabled.

FIGS. 9A, 9B and 9C illustrate top, side cross-sectional and back views of an alternative embodiment of the locking mechanism 110 according to some embodiments. FIG. 9D illustrates a front perspective view of an alternative embodiment of the locking mechanism 110 of FIGS. 9A-C according to some embodiments. The device 100 of FIGS. 9A-D is able to be substantially the same as the device in FIG. 1 except for the differences described herein. As shown in FIGS. 9A, 9B and 9C, the locking mechanism 110 comprises a flexible rod 902 that slides into a slot 904 built into the body 102 of the device 100. In particular, a front side of the body 102 has a cavity 908 adjacent to the positioning component 108 with the slot 904 extending from the top of the body 102 through the cavity 908 and into (at least partially) the bottom of the body 102. As a result, the flexible rod 902 is able to slide into the slot 904 such that the flexible rod 902 is in contact with the side of the positioning component 108. At the same time, similar to FIG. 8, instead of being circular and/or smooth, the outer perimeter surface 906 of the positioning component 108 (adjacent to the rod 902) is able to comprise a plurality of flat faces such that the perimeter 906 is hexagonal, octagonal, or any number of flat faces. Further, each of the flat faces are able to be parallel and/or in contact with the rod 902 when the positioning component 108 is rotated such that the face is the closest to the rod 902. As a result, the rod 902 is able to bias the positioning component 108 into positions where one of the faces is parallel to the rod 902 by pushing against the corners of the perimeter 906 when one of the faces is non-parallel to the rod 902. In particular, as the positioning component 108 rotates and one of the faces begins to move from parallel to the rod 902 to increasingly non-parallel to the rod 902, the corner formed by two of the faces pushes the rod 902 away from the positioning component 108 (into the cavity 908) and the rod 902 resists this movement thereby resisting the rotation of the positioning component 108. Is some embodiments, like in FIG. 3, the rod 902 is able to have a bump and the faces of the perimeter 906 are able to have matching dimples or the rod 902 is able to have a dimple and the faces of the perimeter 906 are able to have matching bumps. This further increases the biasing effect of the rod 902 into the parallel positions where the bump and dimples are aligned. Alternatively, in such embodiments, the perimeter 906 is able to instead be circular or smooth because the dimples/bumps are able to replace the flat faces.

Alternatively, as shown in FIG. 9D, the rod 902, slot 904 and cavity 908 to be positioned adjacent to the front face of the positioning component 108 (but offset from the center of the component 108) instead of the side as in FIGS. 9A-C. In particular, the positioning component 108 is able to be shorter and/or sunk into the body 102 to make room for the rod 902, slot 904 and cavity 908 to be positioned adjacent to the front face of the positioning component 108 instead of the side. In some embodiments, like in FIG. 3, the rod 902 is able to have a bump and a circle on the front face 910 of the component 108 is able to have matching dimples or the rod 902 is able to have a dimple and the circle of the face 910 is able to have matching bumps. As a result, like in FIGS. 9A-9C, the rod 902 is able to bias the positioning component 108 in positions where a bump aligns with a dimple and resist the rotation of the component 108 away from those positions. In any case, like in FIG. 3, the locking mechanism 110 of FIGS. 9A-9D provides the benefit of incremental rotation points such that an amount of rotation/extension of the plate 104 is more precisely enabled.

Figure 10A:
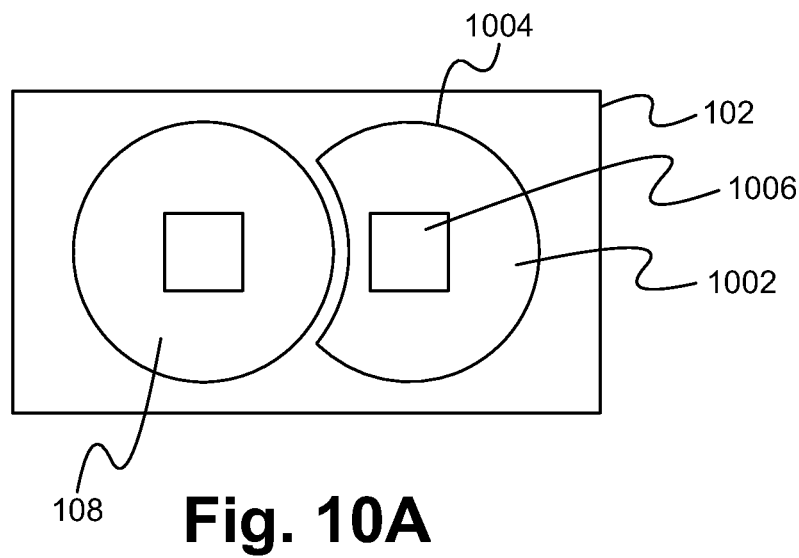
FIG. 10A illustrates a front open view of an alternative embodiment of the locking mechanism according to some embodiments.
Figure 10B:
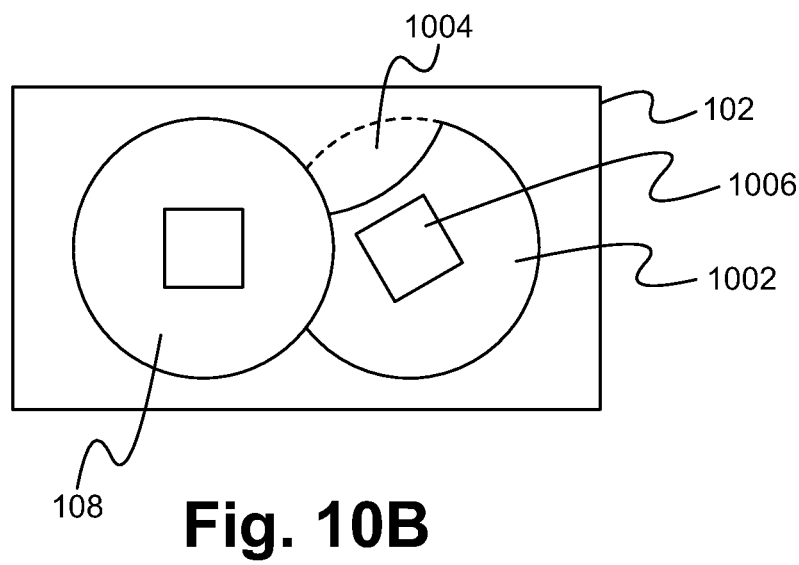
FIG. 10B illustrates a front locked view of an alternative embodiment of the locking mechanism according to some embodiments.

FIGS. 10A and 10B illustrate front open and locked perspective views of an alternative embodiment of the locking mechanism 110 according to some embodiments. The device 100 of FIGS. 10A and 10B is able to be substantially the same as the device in FIG. 1 except for the differences described herein. As shown in FIGS. 10A and 10B, the locking mechanism 110 comprises a rotatable locking cap 1002 positioned in a cap cavity 1004 of the body 102 of the device 100 adjacent to the positioning component 108. Specifically, the locking cap 1002 is able to be a cylinder having a cutout portion such that in an unlocked position, as shown in FIG. 10A, the surface of the cutout portion of the cap 1002 is adjacent to and aligns with the outer surface of the positioning component 108 as it rotates (without impeding the rotation of the component 108). However, when the locking cap 1002 is rotated within the cavity 1004 (e.g. using a cap aperture 1006) such that the cutout portion no longer aligns with the outer surface of the positioning component 108, in a locked position as shown in FIG. 10B, the cap 1002 presses against the outer surface of the positioning component 108 thereby preventing the positioning component 108 from rotating. In some embodiments, the locking cap 1002 is compressible or flexible such that it compresses or bends slightly when in the locked position. As a result, the locking mechanism 110 of FIGS. 10A and 10B provide the benefit of preventing the positioning component 108 from rotating when in a desired position by locking it by rotating the locking cap 1002.

Figure 11A:
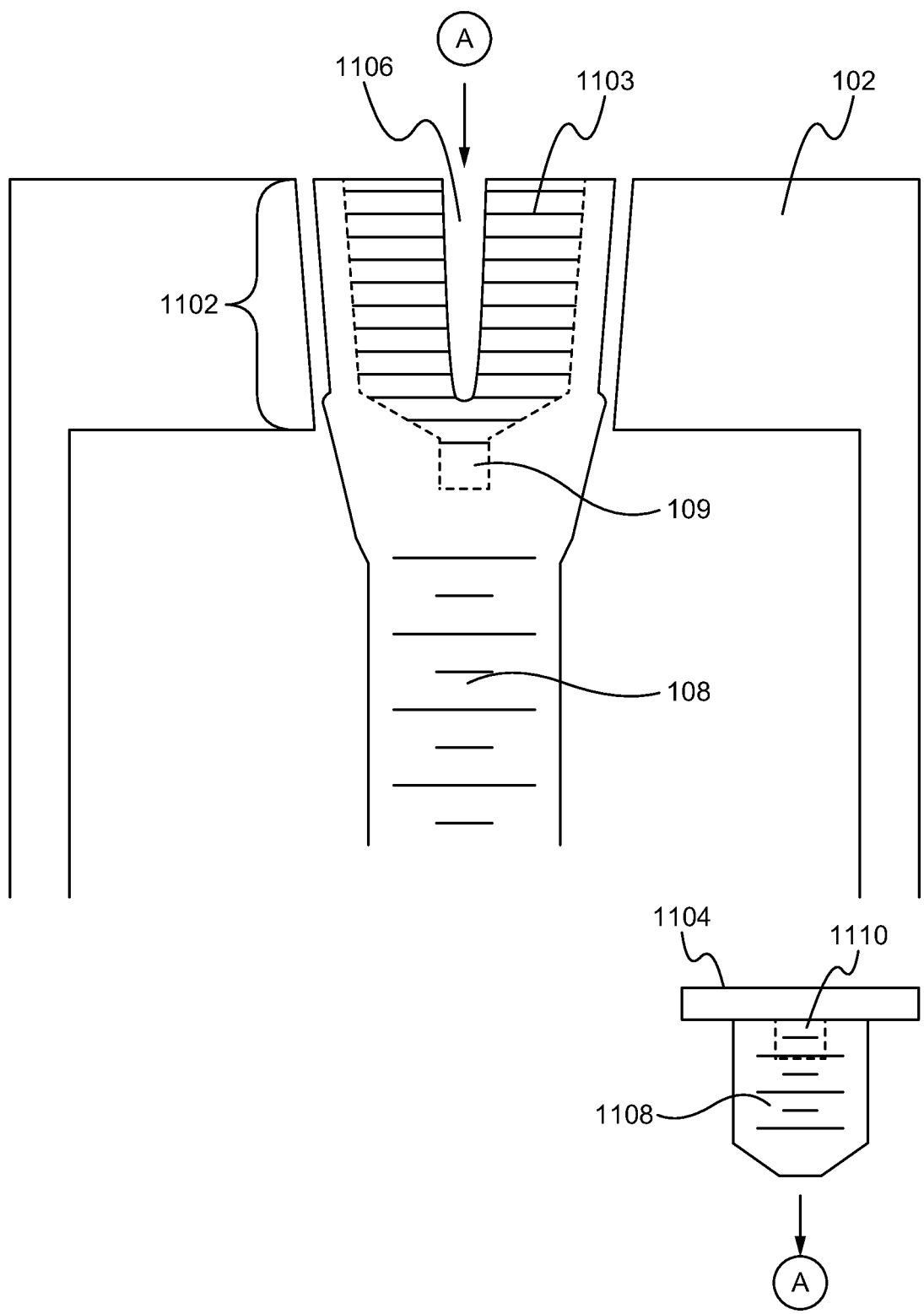
FIG. 11A illustrates a top view of an alternative embodiment of the locking mechanism according to some embodiments.
Figure 11B:
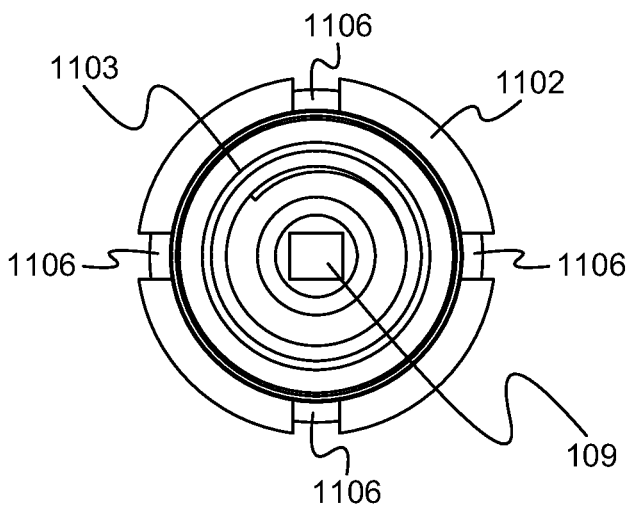
FIG. 11B illustrates a front view of an alternative embodiment of the locking mechanism according to some embodiments.

FIGS. 11A and 11B illustrate top and front perspective views of an alternative embodiment of the locking mechanism 110 according to some embodiments. The device 100 of FIGS. 11A and 11B is able to be substantially the same as the device in FIG. 1 except for the differences described herein. As shown in FIGS. 11A and 11B, the locking mechanism 110 comprises split-collet 1102 coupled to or incorporated into the end of the positioning component 108 and a locking screw 1004. The split-collet 1102 is hollow with a threaded inner surface 1103 and has a plurality of cutouts 1106. The locking screw 1004 has a threaded outer surface 1108, a screw aperture 1110 and a diameter that is greater than the inner diameter of at least a bottom portion of the cavity of the split-collet 1102. As a result, after the positioning component 108 has been rotated to a desired position (e.g. via the aperture 109), using the screw aperture 1110, the locking screw 1004 is able to be screwed into the split-collet 1102 via the threads 1103/1108. As the locking screw 1004 is screwed further into the split-collet 1102, the cutouts 1106 enable the greater diameter of the locking screw 1104 to push the portions of the split-collet 1102 separated by the cutouts 1106 increasingly apart until the bottom of the locking screw 1104 reaches the end of the positioning component 108. This spreading of the portions of the split-collet 1102 causes the split-collet 1102 to push against the inner walls of the body 102 thereby preventing the positioning component 108 from further rotating. As a result, the locking mechanism 110 of FIGS. 11A and 11B provide the benefit of preventing the positioning component 108 from rotating when in a desired position by locking it by rotating the locking screw 1104. Although as shown in FIGS. 11A and 11B the split-collet 1102 has four cutouts 1106, more or less cutouts 1106 are able to be used.

Figure 12A:
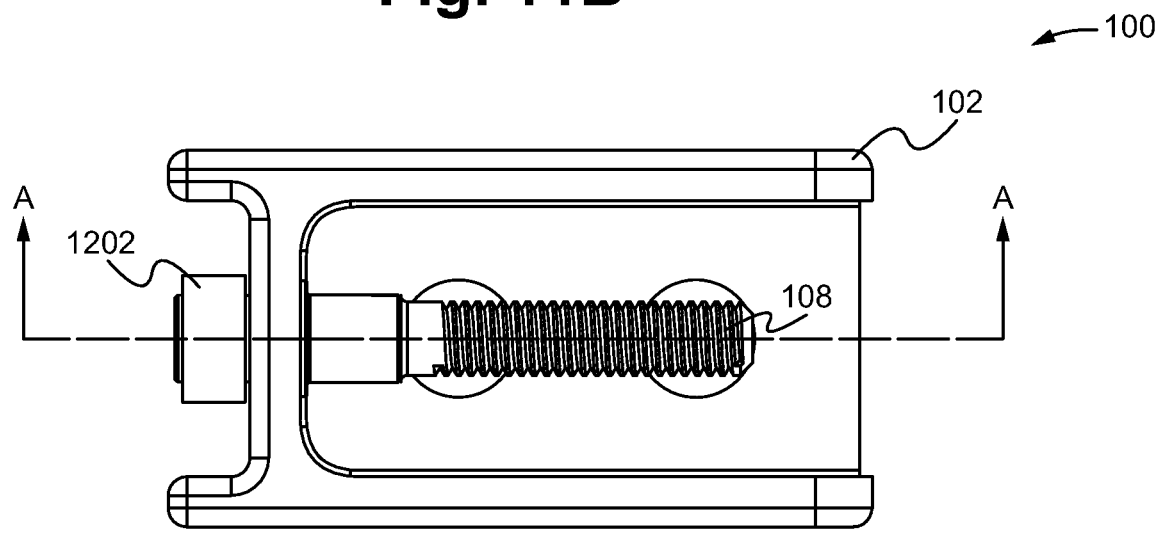
FIG. 12A illustrates a top view of an alternative embodiment of a bone fusion device including a positioning component slide locking mechanism according to some embodiments.
Figure 12B:
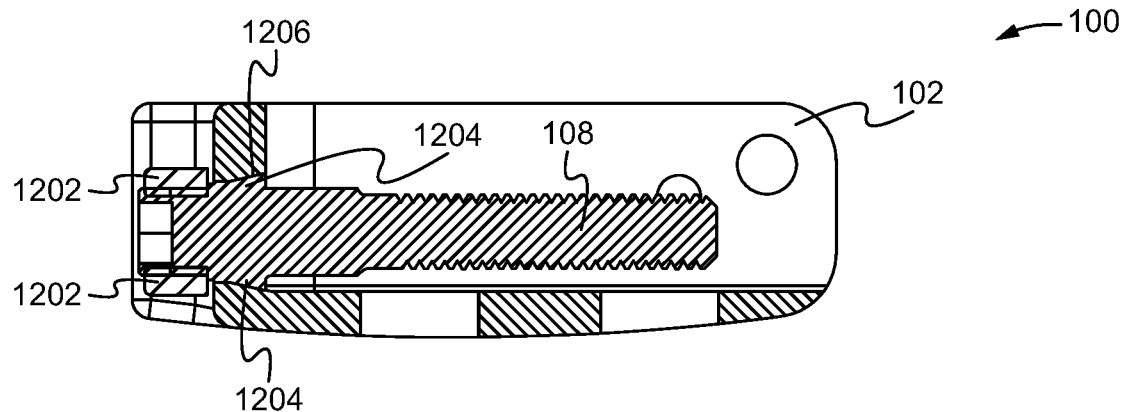
FIG. 12B illustrates a side cross-sectional at the section A-A view of a bone fusion device including a positioning component slide locking mechanism according to some embodiments.

FIGS. 12A and 12B illustrate top and side cross-sectional views of an alternative embodiment of a bone fusion device 100 including a positioning component 108 slide locking mechanism according to some embodiments. The device 100 of FIGS. 12A and 12B is able to be substantially the same as the device in FIG. 1 except for the differences described herein. As shown in FIGS. 12A and 12B, the slide locking mechanism comprises a locking nut 1202 coupled to the head of the positioning component 108, a taper collar 1204 coupled to or a part of the positioning component 108 within the walls of the body 102 and a tapered inner surface 1206 of the front wall of the body 102 (e.g. a part of the hole 308). In particular, when the device 100 is in the extended position (e.g. between two vertebrae), the device 100 is often subject to a compressing/squeezing force that pushes or attempts to push the plate 104 from an extended position back into the retracted position. This force is translated from the plate 104 to the positioning component 108 (via the extending block 112) causing the positioning component 108 to be subject to a force pushing it toward the hole 308 and out of the body 102 (which if it occurred cause failure of the device 100). The taper collar 1204 is able to prevent the positioning component 108 from being pushed out of the body 102 in this manner because its taper resists the pushing by increasingly pressing against the inner wall 1206 of the body 102 as the positioning component 108 is pushed outwards thereby stopping the outward movement. At the same time, the locking nut 1202 prevent the positioning component 108 from sliding too far into the body 102 by blocking the component 108 from fitting through the hole in the front wall of the body 102. In some embodiments, the taper collar 1204 and/or the tapered inner wall of the device 100 have a 3 to 7 degree taper (e.g. 5 degrees). Alternatively, greater or smaller tapers are able to be used.

Figure 4D:
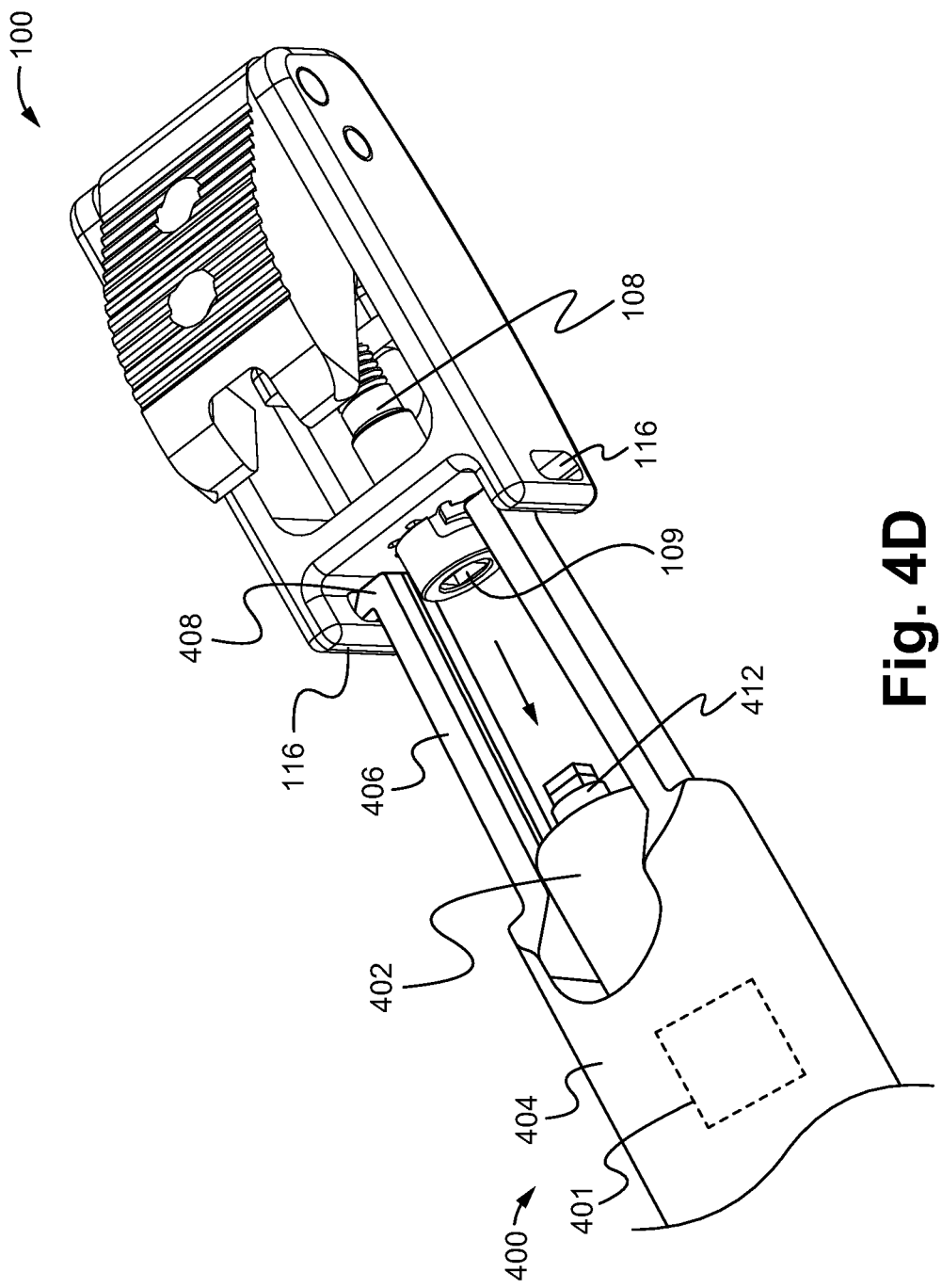
FIG. 4D illustrates a close up perspective view of a bone fusion system having an insertion tool coupled with the bone fusion device according to some embodiments.

FIGS. 4A-D illustrate a side view, top attached view, top unattached view, a close up view, respectively, of a bone fusion system having an insertion tool 400 coupled with the bone fusion device 100 according to some embodiments. As shown in FIGS. 4A-D, the insertion tool 400 comprises a control handle 401 coupled to a rotation rod 402 positioned within a gripping rod 404 having two or more arms 406 protruding from the end of the gripping rod 404. In some embodiments, the gripping rod 404 includes a grip 410 that extends out substantially perpendicular from an axis of the gripping rod 404. The arms 406 are able to angle inwards such that their fingers 408 fit within the space between the coupling rings/hoops 116 when a engaging bit 412 at the tip of the rotation rod 402 is engaged with an aperture 109 of the positioning component 108 (as shown in FIGS. 4A and 4B). For example, hoops 116 are able to be sized to receive the fingers 408 of the arms 406 to prevent the tool 400 from moving laterally with respect to the head of the positioning component 108. Further, due to their inward angle, the inner surfaces of the arms 406 impede the extension of the rotation rod 402 out of the gripping rod 404 toward the device 100.

As a result, when the fingers 408 of the arms 406 are positioned between the hoops 116 and the rotation rod 402 is slid out of the gripping rod 404 by pushing on the control handle 401 and sliding the rotation rod 402 with respect to the gripping rod 404 (as shown in FIGS. 4A and 4B), the outer surface of the rotation rod 402 pushes the arms 406 apart and thus the fingers 408 into the hoops 116 thereby securing the device 100 to the tool 400. Specifically, the pushing of the rotation rod 402 holds the fingers 408 in the hoops 116 such that the fingers 408 cannot exit the hoops 116 until the rotation rod 402 is slid back into the gripping rod 404 (as shown in FIGS. 4C and 4D). The tip 412 of the rotation rod 402 mates with the aperture 109 of the positioning component 108 such that a user is able to rotate the positioning component 108 (and extend the tab of the device 100) by rotating the rotation rod 402 via the handle 401. Alternatively, in some embodiments tip 412 is a part of an inner rod within the rotation rod 402 that is able to rotate within the rotation rod 402 independent of the rotation rod 402. As a result, in such embodiments the control handle 401 is first able to secure the tool 400 to the device 100 (and the tip 412 with the aperture 109) by sliding the rotation rod 402 within the control rod 404 toward the device 100. Then the control handle 401 is able to independently rotate the tip 412 (and thereby the positioning component 108) by rotating the inner rod within the rotation rod 402.

In some embodiments, the fingers 408 have angled tips such that even if they are spread farther apart than the distance between the hoops 116, when pressed against the front of the hoops 116, the angled tips cause the fingers 408 to move closer together in order to squeeze in between the hoops 116. In particular, this feature is beneficial to compensate for manufacturing size errors and/or variance in the inward bias of the fingers 408 because it ensure that they still can be inserted into the hoops 116. In some embodiments, the fingers 408 are sized such that even when spread to be inserted into the coupling rings 116, the fingers 408 remain within the front or back view perimeter or profile. In other words, at end of the tool 400 that coupled to the device 100, the radius of the insertion tool 400 in a plane orthogonal to the axis of the rotation rod/positioning component is equal to or smaller than a largest radius of the bone fusion device 100 in the plane. As a result, the fingers 408 enable the tool 400 and device 100 to maintain a small profile for insertion wherein the profile of the end of the insertion tool 400 is smaller than or equal to the profile of the device 100. In some embodiments, the inserter 400 is able to comprise an encoder/encoding system 401 (e.g. mechanical or electrical) that is able to be communicatively and/or operatively coupled wirelessly or wired to a computer that would read out the position/angle/height of the plate 104 with respect to the body 102 in real time (e.g. based on the amount of rotation of the rotation rod 402 and/or tip 412 after being coupled with the aperture 109 of the positioning component).

In order to release the device 100, the rotation rod 404 is able to be withdrawn back into the gripping rod 404 thereby permitting the arms 406 to spring back inwards and the fingers 208 to slide out of the hoops 116 (as shown in FIGS. 4C and 4D). In some embodiments, the arms 406 are biased inwards such that they automatically spring back to their default inward angle when the rotation rod 402 is not blocking them. As a result, the tool 400 provides the advantage of the arms 406 and/or the gripping rod 404 being within the frontal outline or perimeter of the device 100 such that the incision size to insert the tool 400 with the device 100 does not need to be any bigger to fit the tool 400. Alternatively, the tool 400 is able to comprise an outer tube or ring that surrounds at least part of the gripping rod 404. In such embodiments, the arms 406 are able to have an outwardly angled outer surface such that the outer tube pushes the arms 406 inward when it is slid toward the device 100 thereby sliding the fingers 408 out of the hoops 116. In particular, in such embodiments the arms 406 are able to biased outwards (away from each other) such that they automatically spring back to their default position when the outer tube is not blocking/pushing them inward. Alternatively, a combination of the inward and outward blocking/pushing is able to be used. In some embodiments, the arms 406 are increasingly thicker from the gripping rod 404 to the fingers 408.

Figure 5A:
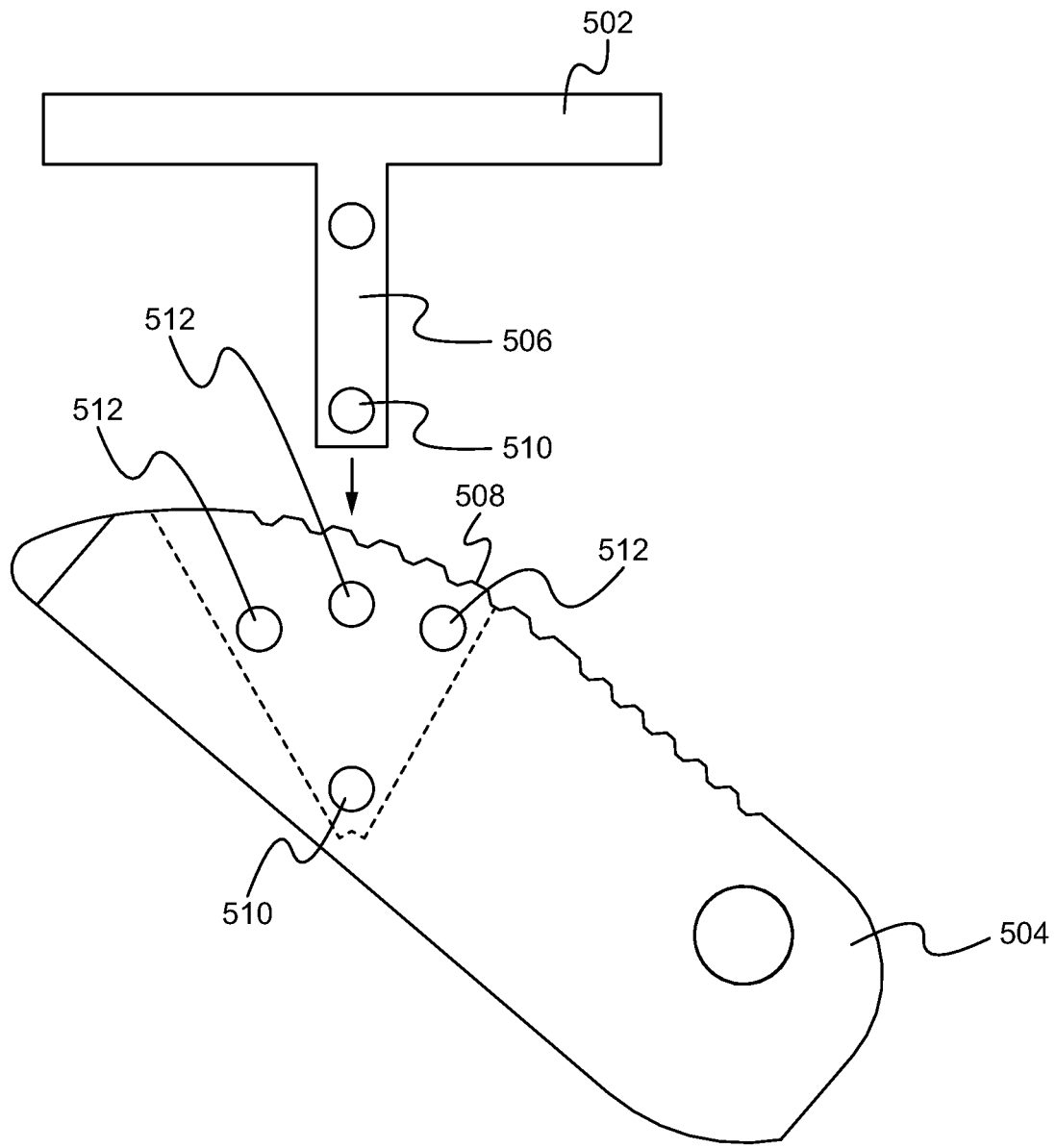
FIG. 5A illustrates a side view of a support platform with a plate for use in a bone fusion device according to some embodiments.
Figure 5B:
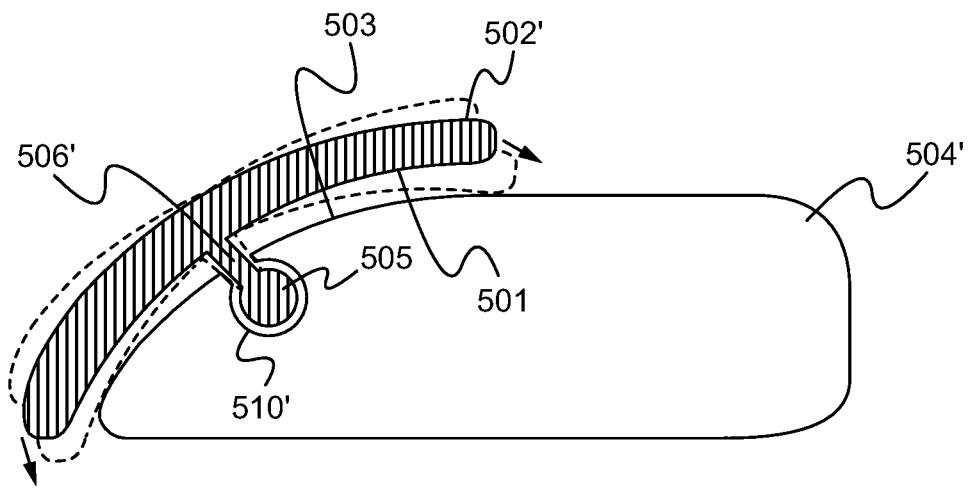
FIG. 5B illustrates a side view of a support platform with a plate for use in a bone fusion device according to some embodiments.

FIG. 5A illustrates a side view of a support platform 502 with a plate 504 for use in a bone fusion device according to some embodiments. The plate 504 is able to be substantially similar to the plate 104 described above except for the differences described herein. As shown in FIG. 5, the platform 502 comprises a coupling base 506 that is configured to slide into a coupling channel 508 of the plate 504. In some embodiments, the plate 504 does not protrude from the body 102 of the device 100 when the plate 504 is in the retracted position. Alternatively, the plate 504 is able to partially or fully protrude above the upper extent of the body 102. Additionally, although in FIG. 5 the base 506 is shown centered under the platform 502, it is able to be off-center and/or at either end of the platform 502. Further, although in FIG. 5A the base 506 is shown perpendicular to the platform 502, it is able to be angled (e.g. any angle between perpendicular and parallel) with the platform 502 and/or the top/upper surface of the platform 502 is able to be curved and/or angled with respect to the bottom surface of the platform 502. In particular, the top/upper surface of the platform 502 is able to be convex to better match an superior inferior vertebral endplate which it contacts. Once within the coupling channel 508, a base holding pin (not shown) is able to be slid through base apertures 510 of the plate 504 and the coupling base 506 thereby securing the platform 504 within the coupling channel 508. Alternatively, as shown in FIG. 5B, the base holding pin is able to be coupled to or a part of the coupling base 506 such that the base aperture 510 of the coupling base 506 is replaced by the base holding pin (e.g. as a protrusion or axle from either end of the coupling base 506 that slides into the base apertures or channel 510 of the plate 504). As a result, the support platform 502 provides the advantage of creating increased surface area for contact with the device 100.

In some embodiments, the channel 508 is able to be shaped such that the platform 502 is prevented from rotating about the holding pin within the channel 508. Alternatively, the channel 508 is able to be shaped to allow the rotation of the platform 502 about the holding pin within the channel 508 (e.g. V-shaped such that the platform 502 is able to rotate about base holding pin between the sides of the V-shape). In some embodiments, the channel 508 is able to be shaped to allow rotation of the platform 502 between a position where the base 506 is parallel with the bottom of the plate 504 to a position where the base 506 is perpendicular to the bottom of the plate 504. Alternatively, the channel 508 is able to be shaped such to allow other ranges of rotation between the base 506 being parallel and being perpendicular to the bottom of the plate 504. In some embodiments, the base 506 comprises at least one and the plate 504 comprises one or more angle apertures 512 for receiving an angle pin that in combination with the base pin secures the platform 502 at a desired angle (e.g. a desired angle within the V-shape). Alternatively, the angle apertures 512 are able to be omitted. As a result, in such embodiments the support platform 502 provides the advantage of enabling adjustment to the angle of contacting surface (e.g. the platform) of the device 100 thereby increasing contact surface area.

Figure 5C:
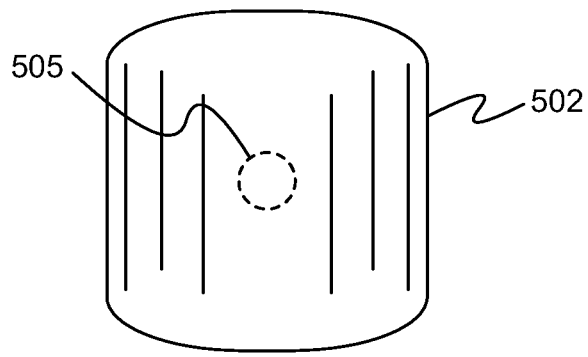
FIG. 5C illustrates a front view of a support platform with a plate for use in a bone fusion device according to some embodiments.
Figure 5D:
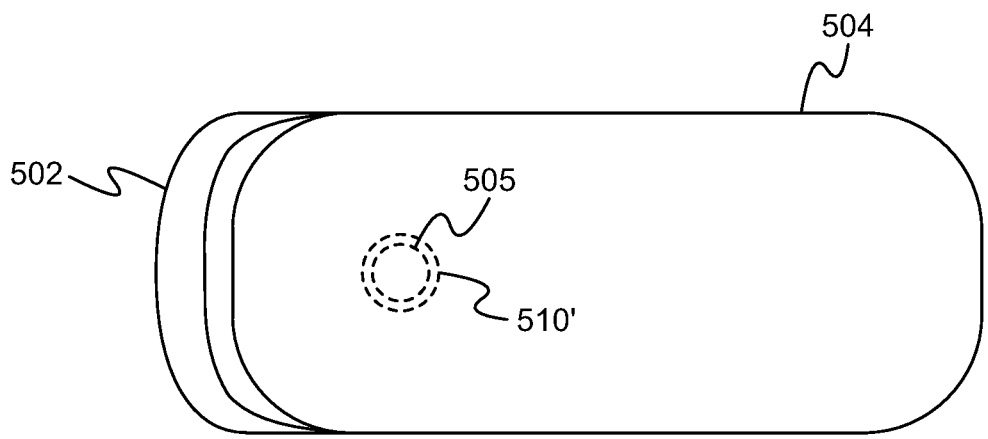
FIG. 5D illustrates a bottom view of a support platform with a plate for use in a bone fusion device according to some embodiments.

FIGS. 5B, 5C and 5D illustrate a side cross-sectional, front, and bottom view, respectively, of a support platform 502' with a plate 504' for use in a bone fusion device according to some embodiments. The plate 504' and platform 502' are able to be substantially similar to the plate 504 and platform 502 described above except for the differences described herein. As shown in FIG. 5B, the platform 502' has a coupling base 506' and a curved bottom surface 501 that matches the curvature of the adjacent upper surface 503 of the plate 504'. As a result, even as the plate 504' is moved toward the extended position and/or the platform 502' rotates (e.g. as indicated by the arrows), the curved surfaces 501, 503 stay substantially adjacent thereby increasing the support provided to the platform 502' from the plate 504'. In particular, due to the maintained adjacency of the surfaces 501, 503, when the platform 502' is subject to a compression force (e.g. by a vertebrae), the bottom surface 501 of the platform 502' contacts the top surface 503 of the plate 504' thereby supporting the platform 502'.

In some embodiments as described above, the base holding pin 505 is able to be coupled to or a part of the coupling base 506' such that the body of the coupling base 506' includes the base holding pin 505. For example, the pin 505 is able to protrude like an axle or tube from either end of the coupling base 506', wherein the pin 505 is sized such that it rotatably fits into the base apertures or channel 510' of the plate 504' (as shown in FIGS. 5G and 5H). Thus, the platform 502' is able to pivot about the axis of the pin 505. Alternatively, the base holding pin 505 is able to be a ball, disk or mass that enables the platform 502' to rotate in multiple directions while within the channel 510'. In either case, the diameter of the pin 505 is greater than the diameter of the "neck" of the coupling base 506' such that the platform 502' is secured to the plate 504' because the pin 505 is unable, but the neck is able to fit through the gap in the channel 510' to the bottom surface 501. In particular, as shown in FIG. 5B, the channel 510 of the plate 504' is sized to receive the base holding pin 505 such that it is able to pivot within the channel 510', but is physically blocked from falling out of the channel 510' due to the surface gap created by the channel 510' being smaller than the diameter of the base holding pin 505.

In some embodiments, the base channel 510' is able to fully extend to one or both sides of the plate 504' (e.g. like a hollow tube) such that the pin 505 is able to be slid into the channel 510' from one or both of the sides (e.g. by inserting an end of the pin 505 into the aperture in the side of the plate 504' created by the channel 510' extending to that side). In some embodiments, the base channel 510 is able to be elongated in a direction parallel to and/or aligned with the top surface 503 of the plate 504' (e.g. a direction from the front of the plate 504' to the back of the plate 504'). Specifically, the extent of the base channel 510' in this direction is able to be greater (e.g. 50, 100, 200 percent) than the extent of the base channel 510' in a perpendicular direction (e.g. a direction perpendicular to the top surface 503 of the plate 504'). Alternatively or in addition, the extent of the base channel 510' in this direction is able to be greater (e.g. 50, 100, 200 percent) than the diameter of the base holding pin 505. As a result, in such embodiments, the base holding pin 505 and/or platform 502' is able to translate within the base channel 510' in addition to rotating as permitted by the elongated dimension of the channel 510' and/or the width of the surface gap through which the coupling base 506' extends to the bottom surface 501'. This provides the advantage of increasing the flexibility of movement of the platform 502' by maximizing contact surface with a bone or other surface when the plate 504' is extended. In some embodiments, the plate 504' comprises a biasing mechanism (e.g a spring) (not shown) that biases the base holding pin 505 to one side of the base channel 510'.

Figure 7A:
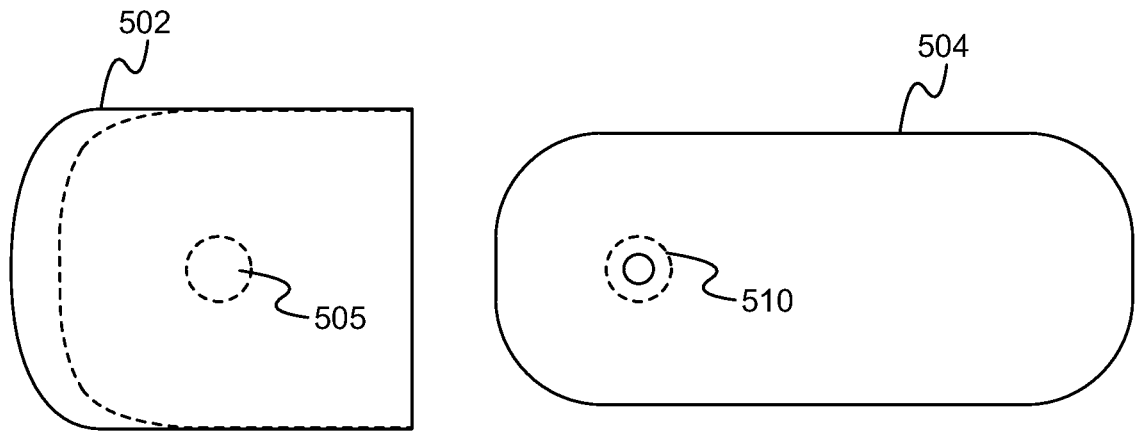
FIG. 7A illustrates a top view of a partial spheroid, ellipsoid or ovoid platform with the plate according to some embodiments.
Figure 7B:
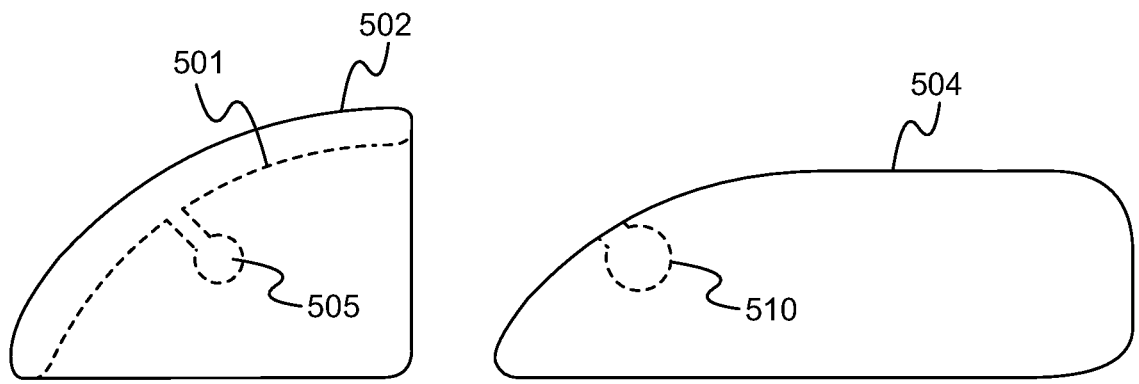
FIG. 7B illustrates a side view of a partial spheroid, ellipsoid or ovoid platform with the plate according to some embodiments.
Figure 7C:
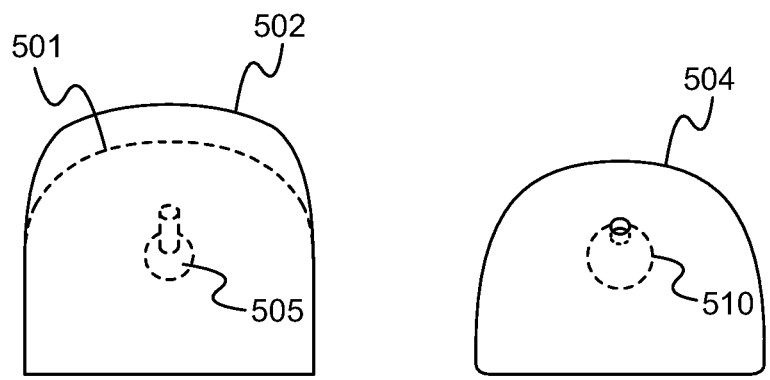
FIG. 7C illustrates a front view of a partial spheroid, ellipsoid or ovoid platform with the plate according to some embodiments.

In some embodiments, the surfaces 501, 503 are curved in the X, Y direction (i.e. in the cross-sectional direction), but substantially flat in the Z direction (e.g. forming a partial tubular or cylindrical surface). Alternatively, as shown in FIGS. 7A-7C, the surfaces 501, 503 are able to be additionally curved in the Z direction (e.g. forming a partial spheroid, ellipsoid or ovoid surface). Specifically, FIG. 7A illustrates a top view of a partial spheroid, ellipsoid or ovoid platform 502 with the plate 504, FIG. 7B illustrates a side view of a partial spheroid, ellipsoid or ovoid platform 502 with the plate 504, and FIG. 7C illustrates a front view of a partial spheroid, ellipsoid or ovoid platform 502 with the plate 504 according to some embodiments. As a result, such embodiments provide the benefit of providing rotation/movement in all directions (due to the curvature of the surfaces) and thereby provide a better contact surface for treating scoliosis.

Figure 5E:
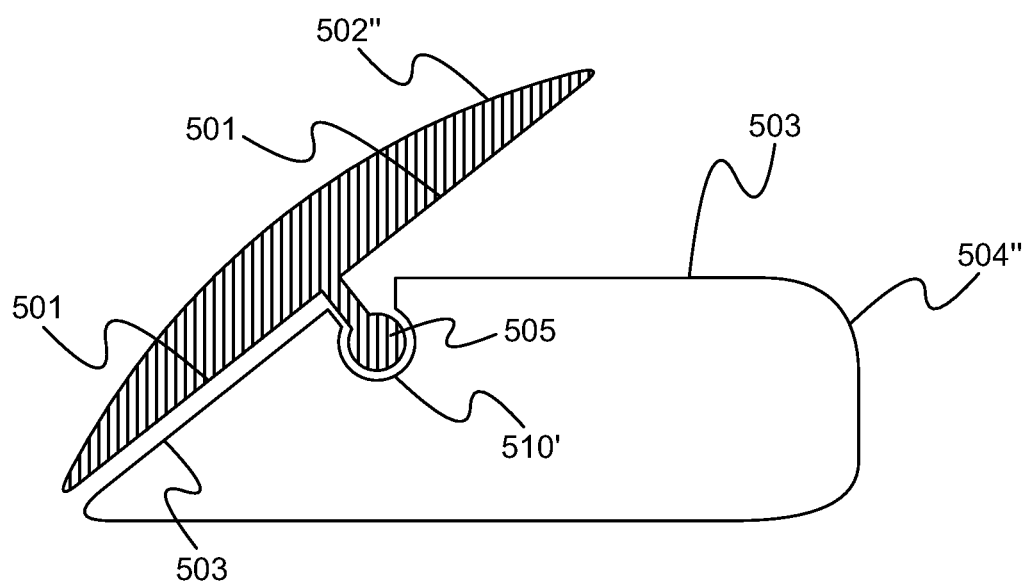
FIG. 5E illustrates a side cross-sectional view of a support platform with a rocking plate for use in a bone fusion device according to some embodiments.
Figure 5F:
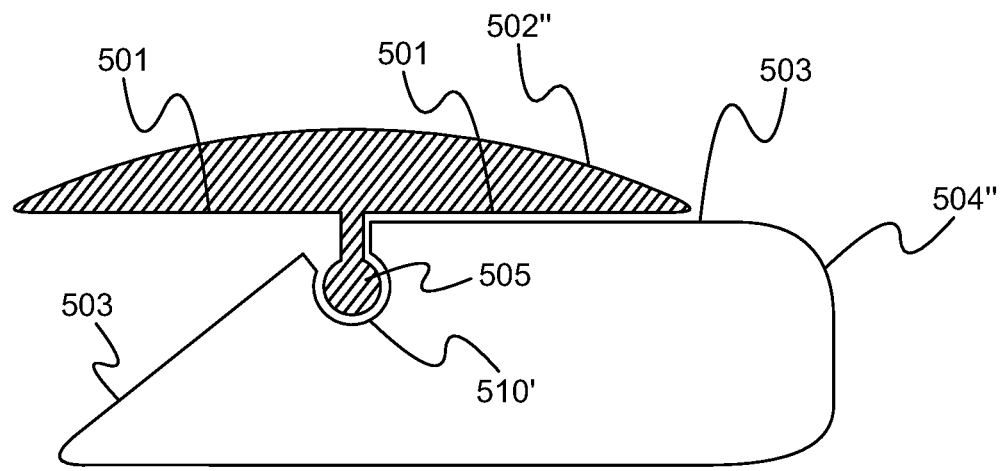
FIG. 5F illustrates a side cross-sectional view of a support platform with a rocking plate for use in a bone fusion device according to some embodiments.
Figure 5G:
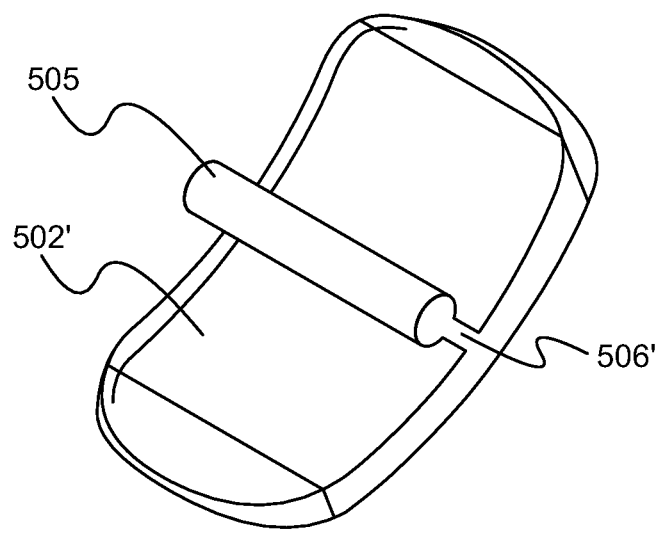
FIG. 5G illustrates a perspective view of a support platform having an axle-like base holding pin according to some embodiments.
Figure 5H:
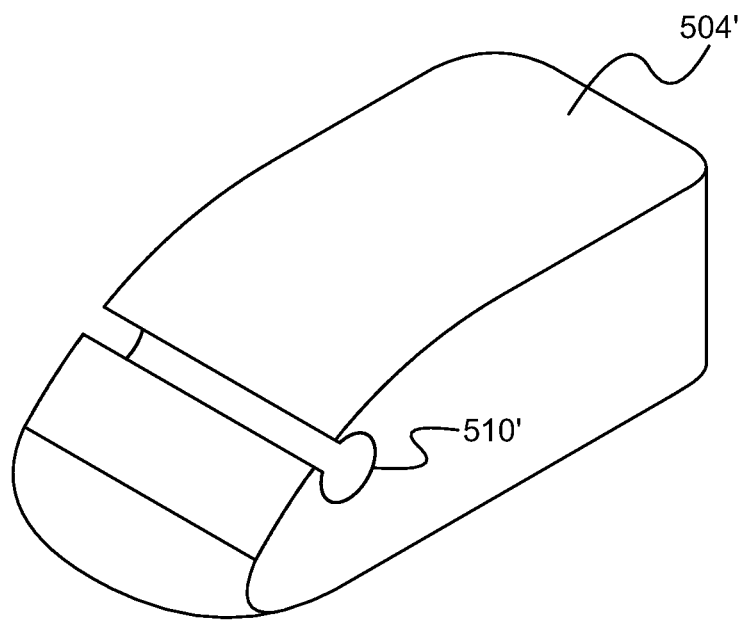
FIG. 5H illustrates a perspective view of a plate having a channel for receiving an axle-like base holding pin of FIG. 5G according to some embodiments.

FIGS. 5E and 5F illustrates a side cross-sectional view of a support platform 502" with a rocking plate 504" for use in a bone fusion device according to some embodiments. The plate 504" and platform 502" are able to be substantially similar to the plate 504' and platform 502' described above except for the differences described herein. As shown in FIGS. 5E and 5F, the plate 504" has an angled front surface 507 that drops below the bottom surface 501 of the platform 502" such that the platform 502" is able to rock about the pin 505 between an upright position where the bottom surface 501 contacts a flat portion (e.g. parallel to the bottom of the plate 504") of the top surface 503 (as shown in FIG. 5E) and an angled position where the bottom surface 501 contacts an angled portion (e.g. non-parallel to the bottom of the plate 504") of the top surface (as shown in FIG. 5F). As a result, in such embodiments the support platform 502" provides the advantage of enabling adjustment to the angle of contacting surface (e.g. the platform) of the device 100 thereby increasing contact surface area.

In some embodiments, the plate 504" further comprises a biasing mechanism (e.g. a spring) that biases the platform 502" in either the upright or the angled position. In some embodiments, the platform 502" of the plate 504" does not protrude from the body 102 of the device 100 when the plate 504" is in the retracted position. Alternatively, the platform 502" of the plate 504" is able to partially or fully protrude above the upper extent of the body 102.

Figure 6:
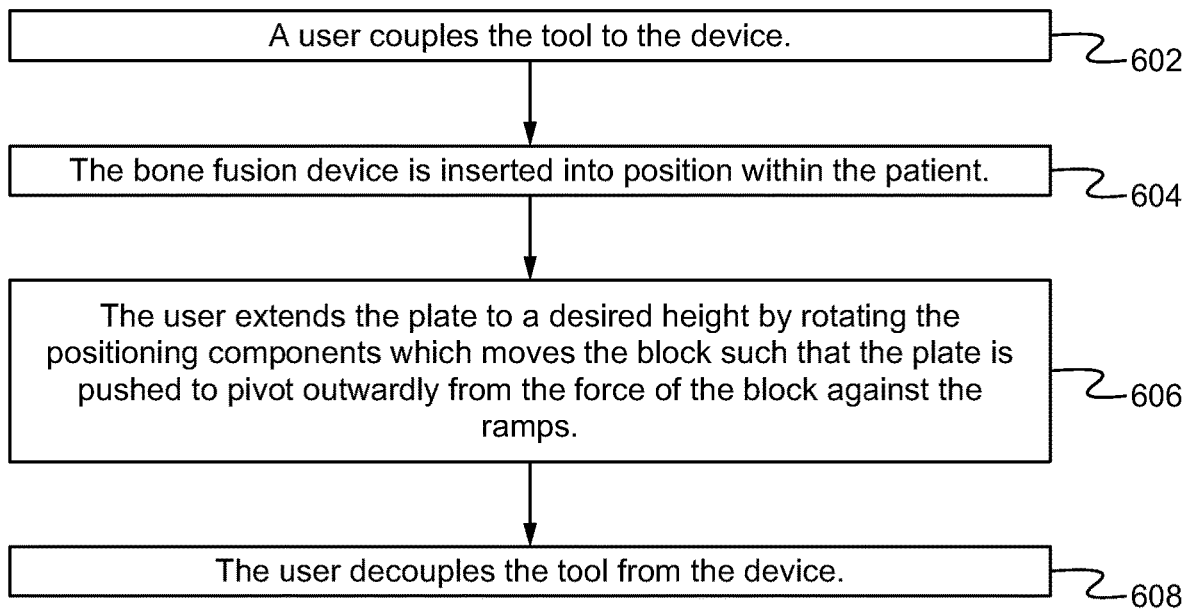
FIG. 6 illustrates a method of using a bone fusion device according to some embodiments.

FIG. 6 illustrates a method of operating a bone fusion device 100 according to some embodiments. As shown in FIG. 6, a user couples the tool 400 to the device 100 at the step 602. In some embodiments, the coupling comprises positioning the arms 406 of the tool 400 between the hoops 116 of the device 100 and sliding the rotation rod 402 toward the device 100 such that the fingers 408 are pushed into the hoops 116 and the rotation rod 402 is engaged with the positioning component 108. In some embodiments, the coupling comprises sliding the outer tube toward the device 100 such that the arms 406 are pushed together, positioning the arms 406 of the tool 400 between the hoops 116 of the device 100 and then retracting the outer ring such that the arms 506 spring outwards and the fingers 408 are pushed into the hoops 116 while the rotation rod 402 is engaged with the positioning component 108. Alternatively, the coupling comprises a combination of the embodiments. The bone fusion device 100 is able to be initially configured in the retracted position such that the plate 104 is fully within the body 102. The bone fusion device 100 is inserted into position within the patient at the step 604. The user extends the plate 104 to a desired height by rotating the positioning component 108 which moves the block 112 such that the plate 104 is pushed to pivot outwardly from the force of the block 112 against the ramps 114 at the step 606. The user decouples the tool 400 from the device 100 at the step 608. As a result, the method provides the advantage of enabling an extension of twice the height of the device 100 while still minimizing the incision size required for insertion.

In some embodiments, the decoupling is able to comprise the reverse of the coupling process used as described above. In some embodiments, the method further comprises providing material for fusing bones together (e.g. bone graft material) through the openings 120 and/or though the gap between the plate 104 and the body 104 as the plate 104 is extended within the bone fusion device 100. Alternatively, the insertion of the material is able to be omitted. In some embodiments, the method further comprises coupling a support platform 502 to the plate 104 in one of the manners described above with reference to FIGS. 5 and 7. In some embodiments, the method further comprises locking the positioning component 108 in place by one or more of applying a biasing force to keep the positioning component 108 in a desired position via a spring 802 or a rod 902. In some embodiments, the method further comprises locking the positioning component 108 in place by one or more of rotating a locking cap 1002 into a locking position and screwing a locking screw 1004 into the split-collet 1102 of the positioning component 108.

Thus, the bone fusion device, system and method described herein has numerous advantages. First, it provides the advantage of enabling large amounts of bone graft or other material to be inserted into the cavity of the body (e.g. before insertion, via the insertion tool; and/or via other tools) due to the large opening created by the rotation/extension of the plate out of the body about the pin. Second, the bone fusion device. provides the advantages of a compact assembly that is suitable for insertion into the patient's body through a open, or minimally invasive surgical procedure. Third, the tool provides the advantage of the arms and/or the gripping rod being within the frontal outline or perimeter of the device such that the incision size to insert the tool with the device does not need to be any bigger to fit the tool. Also, the bone fusion device, system and method provide the advantage of substantially matching the device profiles with the horizontal profiles of the bones to be fused via adjustable support platforms thereby increasing the strength and efficiency of the fusion process. Additionally, the top curvature of the plate 104 provides the advantage of maintaining a substantially parallel topmost surface even as it rotates about the pin. Further, the lock mechanism is able to provide the benefit of enabling the positioning component and thus the plate to be locked in place thereby reducing the risk of the tabs undesirably retracting. The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention.

What is claimed is:

1. A bone fusion device for insertion into a desired location comprising:
   a body having an interior cavity;
   a plate having a first end that is pivotably coupled to a back end of the body at a pivot point, and a second end that is opposite the first end, wherein a top surface of the plate is curved between the first end and the second end and the plate is configured to selectively move from a retracted position having the second end within the interior cavity to an extended position having the second end outside of the interior cavity by pivoting about the pivot point;
   a positioning component located partially within the interior cavity, wherein the positioning component has a central axis and is configured to rotate about the central axis while within the interior cavity; and
   an extending block coupled with the positioning component and configured to slide within the interior cavity of the body based on rotation of the positioning component thereby causing the plate to pivot about a pivot axis between the retracted position and the extended position;
   wherein when in the retracted position, in a direction perpendicular to the central axis and the pivot axis, a minimum distance between the central axis and the top surface of the plate at the second end is smaller than a minimum distance between the central axis and the top surface of the plate at the first end.

2. The device of claim 1, further comprising a locking mechanism coupled to the positioning component adjacent to a front wall of the body and having a biasing spring that contacts a perimeter of the positioning component and biases the positioning component into one of a plurality of discrete positions.

3. The device of claim 1, further comprising a locking mechanism coupled to the positioning component adjacent to the front wall and having a biasing rod that contacts a perimeter of the positioning component and biases the positioning component into one of a plurality of discrete positions.

4. The device of claim 1, further comprising a locking mechanism coupled to the positioning component adjacent to the front wall and having a biasing rod that contacts a front face of the positioning component and biases the positioning component into one of a plurality of discrete positions.

5. The device of claim 1, further comprising a locking mechanism including a split-collet coupled to an end of the positioning component and a locking screw, wherein the locking screw is configured to screw into the split-collet causing the split- collet to expand against the body thereby locking the positioning component from rotating.

6. The device of claim 1, further comprising a locking mechanism including a locking cap rotatably coupled with the front wall of the body and having a cutout portion that aligns with the outer surface of the positioning component when in an unlocked position, wherein when rotated to a locked position, the locking cap presses against the positioning component thereby preventing the positioning component from rotating.

7. The device of claim 1, further comprising a slide locking mechanism including a locking nut coupled around a portion of the positioning component that protrudes outside the body and a tapering collar positioned around a portion of the positioning component within the body, wherein the tapering collar is tapered such that a thickness of the tapering collar decreases from a first end facing inside the body to a second end facing outside the body opposite the first end.

8. A bone fusion device for insertion into a desired location comprising:
- a body having an interior cavity;
- a plate having a first end that is pivotably coupled to a back end of the body at a pivot point and a second end that is opposite the first end, wherein the plate is configured to selectively move from a retracted position having the second end within the interior cavity to an extended position having the second end outside of the interior cavity by pivoting about the pivot point;
- a positioning component located partially within the interior cavity;
- an extending block coupled with the positioning component and configured to slide within the interior cavity of the body based on rotation of the positioning component thereby causing the plate to pivot between the retracted position and the extended position; and
- a support platform including a base stem coupled to a supporting sheet, wherein the base stem pivotably couples within a base channel within the plate such that the support platform protrudes out of the base channel adjacent a top surface of the plate, further wherein the pivot point has a central axis and a width of the supporting sheet in a direction parallel to the central axis is greater than a width of the base channel in the direction.

9. The device of claim 8, wherein the base channel includes a tubular cavity having an axis that is parallel to an axis of the pivot point about which the plate pivots and the base stem comprises an axle positioned at an end of the stem opposite the supporting sheet within the tubular cavity.

10. The device of claim 8, wherein a top of the supporting sheet is rounded and a bottom of the supporting sheet coupled to the base stem is flat.

11. The device of claim 8, wherein a top of the supporting sheet is convex and a bottom of the supporting sheet coupled to the base stem is concave.

12. A bone fusion device for insertion into a desired location comprising:
- a body having an interior cavity;
- a plate having a first end that is pivotably coupled to a back end of the body at a pivot point and a second end that is opposite the first end, wherein the plate is configured to selectively move from a retracted position having the second end within the interior cavity to an extended position having the second end outside of the interior cavity by pivoting about the pivot point;
- a positioning component located partially within the interior cavity;
- an extending block coupled with the positioning component and configured to slide within the interior cavity of the body based on rotation of the positioning component thereby causing the plate to pivot between the retracted position and the extended position; and
- a support platform including a base stem coupled to a supporting sheet, wherein the base stem pivotably couples within a base channel within the plate such that the support platform protrudes out of the base channel adjacent a top surface of the plate, wherein the base stem comprises a ball positioned at an end of the stem opposite the supporting sheet within the base channel, wherein the ball has a diameter that is greater than a diameter of an entrance of the channel formed in an outer surface of the plate.

13. A bone fusion device for insertion into a desired location comprising:
- a body having a front wall and an interior cavity, wherein the front wall includes a positioning aperture surrounded by one or more lock indentations;
- a plate pivotably coupled to the body and configured to selectively move from a retracted position within the interior cavity to an extended position at least partially outside of the interior cavity;
- a positioning component extending through the positioning aperture partially within the interior cavity;
- an extending block coupled with the positioning component and configured to slide within the interior cavity of the body based on rotation of the positioning component about a central axis thereby causing the plate to move between the retracted position and the extended position; and
- a locking mechanism coupled to the positioning component adjacent to the front wall and having a locking arm with a protruding locking tip that protrudes from the locking arm in the direction of the central axis, wherein the lock indentations extend into the front wall in the direction of the central axis and the locking arm biases the locking tip in the direction of the central axis such that when aligned with one of the lock indentations the locking tip slides into the one of the lock indentations and thereby resists rotation of the positioning component, wherein the protruding locking tip has an angled leading edge with respect to the front wall that facilitates the sliding of the locking tip out of the lock indentations and a flat trailing edge that resists the sliding of the locking tip out of the lock indentations.

* * * * *